United States Patent
Bibova et al.

(10) Patent No.: US 11,643,413 B2
(45) Date of Patent: May 9, 2023

(54) 9-(2-OXACYCLOALKYL)-9H-PURINE-2,6-DIAMINE DERIVATIVES AND THEIR USE FOR THE TREATMENT OF SKIN DISORDERS

(71) Applicant: UNIVERZITA PALACKEHO V OLOMOUCI, Olomouc (CZ)

(72) Inventors: Jana Bibova, Opava (CZ); Vaclav Mik, Grygov (CZ); Marek Zatloukal, Sumperk (CZ); Lucie Plihalova, Olomouc (CZ); Jiri Gruz, Bohunovice (CZ); Lukas Spichal, Olomouc (CZ); Karel Dolezal, Hlubocky (CZ); Miroslav Strnad, Olomouc (CZ)

(73) Assignee: UNIVERZITA PALACKEHO V OLOMOUCI, Olomouc (CZ)

( * ) Notice: Subject to any disclaimer, the term of this patent is extended or adjusted under 35 U.S.C. 154(b) by 314 days.

(21) Appl. No.: 16/604,494

(22) PCT Filed: Apr. 27, 2018

(86) PCT No.: PCT/CZ2018/050021
§ 371 (c)(1),
(2) Date: Oct. 10, 2019

(87) PCT Pub. No.: WO2018/196893
PCT Pub. Date: Nov. 1, 2018

(65) Prior Publication Data
US 2020/0157105 A1    May 21, 2020

(30) Foreign Application Priority Data

Apr. 28, 2017 (CZ) ................ CZ2017-237

(51) Int. Cl.
| | | |
|---|---|---|
| C07D 473/16 | (2006.01) |
| A61K 31/505 | (2006.01) |
| A61K 31/52 | (2006.01) |
| A61K 31/22 | (2006.01) |
| A61Q 19/08 | (2006.01) |
| A61Q 19/00 | (2006.01) |
| A61P 17/00 | (2006.01) |
| A61P 25/00 | (2006.01) |
| A61P 35/00 | (2006.01) |
| A61P 37/00 | (2006.01) |
| A61P 39/06 | (2006.01) |
| A61K 8/49 | (2006.01) |

(52) U.S. Cl.
CPC .......... *C07D 473/16* (2013.01); *A61K 8/4953* (2013.01); *A61Q 19/08* (2013.01)

(58) Field of Classification Search
CPC .... C07D 473/16; A61K 8/4953; A61K 8/494; A61K 31/505; A61K 31/52; A61K 31/22; A61Q 18/00; A61Q 18/08; A61P 17/00; A61P 25/00; A61P 35/00; A61P 37/00; A61P 39/06
See application file for complete search history.

(56) References Cited

U.S. PATENT DOCUMENTS

2008/0009508 A1    1/2008  Szucova et al.

FOREIGN PATENT DOCUMENTS

WO        03040144 A2    5/2003

OTHER PUBLICATIONS

Verdugo et al., 2001, caplus an 2001:514513.*
AlzheimersDisease, 2023, https://www.mayoclinic.org/diseases-conditions/alzheimers-disease/diagnosis-treatment/drc-20350453.*
Melkerson et al., 2023, https://pubmed.ncbi.nlm.nih.gov/15025545/.*
Szucova L et al: "Synthesis, characterization and biological activity of ring-substituted 6-benzylamino-9-tetrahydropyran-2-yl and 9-tetrahydrofuran-2-ylpurine derivatives", Bioorganic & Medicinal Chemistry, Pergamon, GB, vol. 17, No. 5, Mar. 1, 2009 (Mar. 1, 2009), pp. 1938-1947.
International Search Report and Written Opinion for corresponding PCT application PCT/CZ2018/050021, dated Jul. 17, 2018.

* cited by examiner

*Primary Examiner* — Sun Jae Yoo
(74) *Attorney, Agent, or Firm* — Notaro, Michalos & Zaccaria P.C.

(57) ABSTRACT

The invention relates to $N^2,N^6$-disubstituted-9-(2-oxacycloalkyl)-9H-purine-2, 6-diamine derivatives and their use as drugs and cosmetics. The compounds of the present invention exhibit a number of biological activities associated with oxidative stress inhibition, especially anti-aging, anti-inflammatory and anti-neurodegenerative biological activities. The invention also relates to cosmetic and pharmaceutical compositions containing such derivatives as active agents.

12 Claims, 1 Drawing Sheet

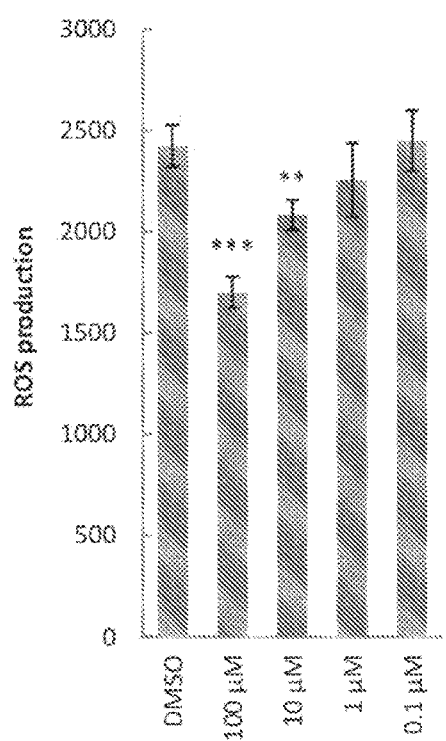

9-(2-OXACYCLOALKYL)-9H-PURINE-2,6-DIAMINE DERIVATIVES AND THEIR USE FOR THE TREATMENT OF SKIN DISORDERS

TECHNICAL FIELD

The invention relates to $N^2,N^6$-disubstituted-9-(2-oxacycloalkyl)-9H-purine-2,6-diamine derivatives, their use in cosmetic and medicinal applications and compositions containing these derivatives.

BACKGROUND ART

Generally, natural cytokinins are $N^6$-substituted adenine derivatives. The first cytokinin to be identified was kinetin (K, $N^6$-furfuryladenine), which was isolated and identified in 1955 as a degradation product of DNA that promotes cell division in plants. Kinetin is believed to be an artefactual cytokinin that originates from the autoclaving of herring-sperm DNA or forms on DNA storage over a long period of time. Kinetin as well as other cytokinins can be further substituted at position C2, N3, N7 and N9 on purine ring. The most frequent are N9-nucleosides and nucleotides. The chemical structure of kinetin clearly indicates that the reaction of an adenine residue of DNA with furfural may be the possible synthetic pathway. Recent experiments show that furfural, which is the oxidized sugar residue, is formed during oxidative damage to DNA in vitro. Furfural originates from hydroxyl radical oxidation of the deoxyribose residue at the carbon 5' and reacts with the amino group of adenine, consequently forming the Schiff base. Another intramolecular rearrangement yields kinetin in vivo (Barciszewski et al. FEBS Lett 414:457-460, 1997). These findings indicate that kinetin is an important component of a new salvage pathway of hydroxyl radicals constituting a 'free radical sink,' which is in compliance with the hypothesis that cytokinins are products of the oxidative metabolism of the cell. This is how cells neutralize the harmful properties of reactive oxygen species (ROS) and respond to oxidative stress by inducing the molecular mechanisms of defense and repair (Barciszewski et al. Int J Biol Macromol 40:182-192, 2007). Recently, the effect of $N^6$-benzyladenine and kinetin on basic oxidative stress parameters, such as antioxidative enzyme activity, reduced glutathione and thiol group content, and lipid peroxidation have been shown (Jablonska-Trypuc' et al. Mol Cell Biochem 413:97-107, 2016). Four natural $N^6$-substituted adenine derivatives (cytokinins) were evaluated for the first time in vitro for their antioxidant capacity using fluorimetric and spectrophotometric assays, i.e., the oxygen radical absorbance capacity (ORAC), trolox equivalence antioxidant capacity (TEAC) and the 2-deoxyribose degradation (2-DRA) assays (Brizzolari et al. J. Chromatogr. B 1019: 164-168, 2016).

For the past 40 years or so, oxidative stress has been increasingly recognized as a contributing factor in aging and in various forms of pathophysiology generally associated with aging. Our view of oxidative stress has been largely "superoxide-centric", as we focused on the pathological sources of this oxygen-derived free radical and the types of molecular havoc it can wreak, as well as on the protection provided by the antioxidant enzymes, especially the superoxide dismutases, catalases, and glutathione peroxidases. In the last decade our view of oxidative stress has broadened considerably, and it is now often seen as an imbalance that has its origins in our genes, and the ways in which gene expression is regulated. At the center of this new focus is the transcription factor called nuclear factor (erythroid-derived 2)-like 2, or Nrf2. Nrf2 is referred to as the "master regulator" of the antioxidant response, modulating the expression of hundreds of genes, including not only the familiar antioxidant enzymes, but large numbers of genes that control seemingly disparate processes such as immune and inflammatory responses, tissue remodeling and fibrosis, carcinogenesis and metastasis, and even cognitive dysfunction and addictive behavior. Thus, the dysregulation of Nrf2-regulated genes provides a logical explanation for the connections, both direct and indirect, between observable oxidative stress and perhaps 200 human diseases involving these various physiological processes, each reflecting a network involving many gene products. The evolutionary self-association of these many genes under the common control of Nrf2 suggests that the immune and inflammatory systems may present the largest demand for increased antioxidant protection, apart from constitutive oxidative stress resulting from mitochondrial oxygen consumption for metabolic purposes (Hybertson et al. Molecular Aspects of Medicine 32 (2011) 234-246).

It is an object of this invention to provide new generation of cytokining analogues showing strong antioxidative properties and/or exhibiting the ability to regulate expression of an important stress transcription factor NRF2. New generation of cytokinin-like compounds are potentially powerful agents with applications in the prevention and treatment of many diseases connected with oxidative stress in skin, for example, skin cancer and psoriasis. Oxidative stress and its processes are also necessary for development of fibrosis in fibrotic disorders such as scleroderma, GVHD, hypertrophic scars, NSF, and other skin pathologies. New generation of cytokinin-like compounds for use to treat skin diseases induced by increased oxidative stress is characterized by improved selectivity and efficiency index, i.e. less toxic and yet more efficacious compounds than analogues known heretofore.

DISCLOSURE OF THE INVENTION

The object of this invention are $N^2,N^6$-disubstituted-9-(2-oxacycloalkyl)-9H-purine-2,6-diamine derivatives of the general formula I,

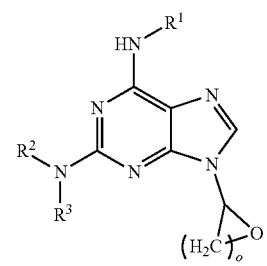

wherein
$R^2$ and $R^3$ are independently selected from H, —$(CH_2)_m$CH_3$, m=0 or 1 or 2, —$CH_2(CH_3)_2$, —$(CH_2)_n$—$N(CH_3)_2$, n=2 or 3,
wherein at least one of R2 and R3 is alkyl or dimethylaminoalkyl;
 o is an integer ranging from 2 to 5, i.e. 2 or 3 or 4 or 5,
  wherein a hydrogen in at least one methylene group (CH2) in the substituent on N9 may be optionally replaced by a methyl or methoxy group, thus the substituent on N9 is selected from the group comprising oxetan-2-yl, tetrahydrofuran-2-yl, tetrahydro-2H-pyran-2-yl or oxepan-2-yl, optionally substituted with at least one methyl or methoxy;

$R^1$ is selected from the group containing furfuryl or furfuryl substituted with at least one, preferably just one, methyl or methoxy group, benzyl or benzyl substituted by at least one substituent, preferably with one or two or three substituents, selected from the group comprising methyl, trifluoromethyl, hydroxy, methoxy, trifluoromethoxy, halogen, amino, methoxycarbonyl and/or acetoxy 3-methylbut-2-en-1-yl 3-methylbut-3-en-1-yl (4-hydroxy-3-methylbut-2-en-1-yl 4-hydroxy-3-methylbutyl and pharmaceutically acceptable salts thereof.

Pharmaceutically acceptable salts are in particular salts with alkali metals, ammonia or amines or addition salts with acids. Preferably, they are pharmaceutically or cosmetically acceptable salts.

In the case of chiral centers in the molecule, the present invention also includes optically active isomers, mixtures thereof and racemates.

Preferably, when $R^2$ or $R^3$ is —$(CH_2)_nN(CH_3)_2$, then the other of these substituents is hydrogen.

Preferably, the group —$N(R^2)(R^3)$ is selected from the group comprising methylamino, ethylamino, propylamino, 2-propylamino, dimethylamino, diethylamino, [2-(dimethylamino)ethyl]amino; [3-(dimethylamino)propyl]amino.

Preferably, the group —$N(R^2)(R^3)$ is selected from the group comprising methylamino, ethylamino, dimethylamino, diethylamino, [2-(dimethylamino)ethyl]amino.

In one preferred embodiment, $R^1$ is selected from the group containing furfuryl, 3-methylfurfuryl, 4-methylfurfuryl, 5-methylfurfuryl, 3-methoxyfurfuryl, 4-methoxyfurfuryl, 5-methoxyfurfuryl, benzyl, 2-methylbenzyl, 3-methylbenzyl, 4-methylbenzyl, 2-(trifluoromethyl)benzyl, 3-(trifluoromethyl)benzyl, 4-(trifluoromethyl)benzyl, 2-hydroxybenzyl, 3-hydroxybenzyl, 4-hydroxybenzylamino, 2-methoxybenzyl, 3-methoxybenzyl, 4-methoxybenzyl, 2-(trifluoromethoxy)benzyl, 3-(trifluoromethoxy)benzyl, 4-(trifluoromethoxy)benzyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 2-iodobenzyl, 3-iodobenzyl, 4-iodobenzyl, 2-aminobenzyl, 3-aminobenzyl, 4-aminobenzyl, 2-(methoxykarbonyl)benzyl, 3-(methoxykarbonyl)benzyl, 4-(methoxykarbonyl)benzyl, 2-acetoxybenzyl, 3-acetoxybenzyl, 4-acetoxybenzyl, 2,3-dihydroxybenzyl, 2,5-dihydroxybenzyl, 3,4-dihydroxybenzyl, 3,5-dihydroxybenzyl, 2,3-dimethoxybenzyl, 2,5-dimethoxybenzyl, 3,4-dimethoxybenzyl, 3,5-dimethoxybenzyl, 2,6-difluorobenzyl, 3,4-difluorobenzyl, 3,5-difluorobenzyl, 2,3-dichlorobenzyl, 2,4-dichlorobenzyl, 3,4-dichlorobenzyl, 3,5-dichlorobenzyl, 2-hydroxy-3-methylbenzyl, 2-hydroxy-5-methylbenzyl, 2-hydroxy-3-methoxybenzyl, 2-hydroxy-4-methoxybenzyl, 3-hydroxy-4-methoxybenzyl, 4-hydroxy-2-methoxybenzyl, 4-hydroxy-3-methoxybenzyl, 3-fluoro-4-hydroxybenzyl, 3-chloro-4-hydroxybenzyl, 4-fluoro-3-hydroxybenzyl, 4-chloro-3-hydroxybenzyl, 2-chloro-4-fluorobenzyl, 2-chloro-6-fluorobenzyl, 3,4,5-trihydroxybenzyl, 3,4,5-trimethoxybenzyl, 2,3,4-trifluorobenzyl, 2,3,6-trifluorobenzyl, 3,4,5-trifluorobenzyl, 4-hydroxy-3,5-dimethoxybenzyl, 3-methylbut-2-en-1-yl, 3-methylbut-3-en-1-yl, 4-hydroxy-3-methylbut-2-en-1-yl, -hydroxy-3-methylbutyl)amino.

Preferably, the substituent on N9 is selected from tetrahydro-2H-pyran-2-yl and tetrahydrofuran-2-yl, which may be optionally substituted with at least one, preferably with one methyl or methoxy group.

In the preferred embodiment, the 9-(2-oxacycloalkyl)-9H-purine-2,6-diamine derivatives of the general formula I are selected from the group comprising:

2-(methylamino, ethylamino, propylamino, 2-propylamino, dimethylamino, diethylamino, [2-(dimethylamino)ethyl] amino, [3-(dimethylamino)propyl]amino)-6-furfurylamino-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl] amino)-6-[(3-methylfurfuryl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-methylfurfuryl)amino]-9-(oxetan-2-yl, tetrahydrofuran-2-yl, tetrahydro-2H-pyran-2-yl, oxepan-2-yl)-9H-purine, 2-(methylamino, ethylamino, propylamino, 2-propylamino, dimethylamino, diethylamino, [2-(dimethylamino)ethyl] amino, [3-(dimethylamino)propyl]amino)-6-[(5-methylfurfuryl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl] amino, [3-(dimethylamino)propyl]amino)-6-(3-methoxyfurfurylamino)-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl] amino, [3-(dimethylamino)propyl]amino)-6-(4-methoxyfurfurylamino)-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl] amino, [3-(dimethylamino)propyl]amino)-6-(5-methoxyfurfurylamino)-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl] amino, [3-(dimethylamino)propyl]amino)-6-benzylamino-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl] amino)-6-[(2-methylbenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-methylbenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl] amino, [3-(dimethylamino)propyl]amino)-6-[(4-methylbenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-{[2-(trifluoromethyl)benzyl] amino}-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-{[3-(trifluoromethyl)benzyl]amino}-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-{[4-(trifluoromethyl)benzyl]amino}-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-hydroxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-hydroxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-hydroxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-methoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-methoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-methoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-{[2-(trifluoromethoxy)benzyl]amino}-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-{[3-(trifluoromethoxy)benzyl]amino}-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-{[4-(trifluoromethoxy)benzyl]amino}-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-fluorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-fluorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-fluorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-chlorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-chlorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-chlorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-bromobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-bromobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-bromobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-iodobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-iodobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-iodobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-aminobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-aminobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-aminobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-{[2-(methoxycarbonyl)benzyl]amino}-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-{[3-(methoxycarbonyl)benzyl]amino}-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-{[4-(methoxycarbonyl)benzyl]amino}-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-acetoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-acetoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-acetoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2,3-dihydroxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2,5-dihydroxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3,4-dihydroxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3,5-dihydroxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2,3-dimethoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2,5-dimethoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3,4-dimethoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3,5-dimethoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2,6-difluorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3,4-difluorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3,5-difluorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2,3-dichlorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2,4-dichlorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3,4-dichlorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3,5-dichlorobenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-hydroxy-3-methylbenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-hydroxy-5-methylbenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-hydroxy-3-methoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(2-hydroxy-4-methoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-hydroxy-4-methoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-hydroxy-2-methoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-hydroxy-3-methoxybenzyl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(3-fluoro-4-hydroxybenzyl)amino]-9-(oxetan-2-yl, tetrahydrofuran-2-yl, tetrahydro-2H-pyran-2-yl, oxepan-2-yl)-9H-purine;

2-(methylamino, ethylamino, propylamino, 2-propylamino, dimethylamino, diethylamino, [2-(dimethylamino)ethyl]amino, [3-(dimethylamino)propyl]amino)-6-[(3-chloro-4-hydroxybenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(4-fluoro-3-hydroxybenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(4-chloro-3-hydroxybenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(2-chloro-4-fluorobenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(2-chloro-6-fluorobenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(3,4,5-trihydroxybenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(3,4,5-trimethoxybenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(2,3,4-trifluorobenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(2,3,6-trifluorobenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(3,4,5-trifluorobenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(4-hydroxy-3,5-dimethoxybenzyl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(3-methylbut-2-en-1-yl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-[(3-methylbut-3-en-1-yl)amino]-9-(oxetan-2-yl, tetrahydrofuran-2-yl, tetrahydro-2H-pyran-2-yl, oxepan-2-yl)-9H-purine;
2-(methylamino, ethylamino, propylamino, 2-propylamino, dimethylamino, diethylamino, [2-(dimethylamino)ethyl]amino, [3-(dimethylamino)propyl]amino)-6-(E)-[(4-hydroxy-3-methylbut-2-en-1-yl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-(Z)-[(4-hydroxy-3-methylbut-2-en-1-yl)amino]-9-(oxetan-2-yl, tetrahydrofuran-2-yl, tetrahydro-2H-pyran-2-yl, oxepan-2-yl)-9H-purine; 2-(methylamino, ethylamino, propylamino, 2-propylamino, dimethylamino, diethylamino, [2-(dimethylamino)ethyl]amino, [3-(dimethylamino)propyl]amino)-6-[(4-hydroxy-3-methylbutyl)amino]-9-(oxetan-2-yl, tetrahydrofuran-2-yl, tetrahydro-2H-pyran-2-yl, oxepan-2-yl)-9H-purine, and the pharmaceutically acceptable salts thereof with alkali metals, ammonium or amines, in the forms of racemates or optically active isomers, as well as their addition salts with acids.

The most preferred $N^2,N^6$-disubstituted 9-(2-oxacycloalkyl)-9H-purine-2,6-diamine derivatives of the general formula I are selected from the group comprising: 2-(methylamino)-6-furfurylamino-9-(tetrahydrofuran-2-yl)-9H-purine, 2-(ethylamino)-6-furfurylamino-9-(tetrahydrofuran-2-yl)-9H-purine; 2-(dimethylamino)-6-furfurylamino-9-(tetrahydrofuran-2-yl)-9H-purine; 2-(diethylamino)-6-furfurylamino-9-(tetrahydrofuran-2-yl)-9H-purine; 2-{[2-(dimethylamino)ethyl]amino}-6-furfurylamino-9-(tetrahydrofuran-2-yl)-9H-purine; 2-(methylamino)-6-furfurylamino-9-(tetrahydro-2H-pyran-2-yl)-9H-purine, 2-(ethylamino)-6-furfurylamino-9-(tetrahydro-2H-pyran-2-yl)-9H-purine; 2-(dimethylamino)-6-furfurylamino-9-(tetrahydro-2H-pyran-2-yl)-9H-purine; 2-(diethylamino)-6-furfurylamino-9-(tetrahydro-2H-pyran-2-yl)-9H-purine; 2-{[2-(dimethylamino)ethyl]amino}-6-furfurylamino-9-(tetrahydro-2H-pyran-2-yl)-9H-purine, and their salts, wherein the furfuryl group can optionally be substituted with at least one substituent selected from the group comprising methyl or methoxy group.

The $N^2,N^6$-disubstituted-9-(2-oxacycloalkyl)-9H-purine-2,6-diamine derivatives according to the present invention have a wide range of biological activities, including antioxidant, anti-senescent, antiaging, and pro-differentiation activities, which are especially useful in pharmaceutical and cosmetic applications (e.g. to treat skin diseases). The compounds according to the present invention (and compositions containing thereof) possess antioxidant, pro-differentiating, antisenescent and antiaging properties with improved selectivities and efficiencies and minimal or zero toxicities comparing to their analogues known in the state of the art.

The object of the present invention are also $N^2,N^6$-disubstituted-9-(2-oxacycloalkyl)-9H-purine-2,6-diamine derivatives of the general formula I for use in the cellular defense either in vivo or in vitro against oxidative or electrophilic stress for inhibiting improper and unsatisfactory metabolic processes in mammals and plants.

Nrf2-antioxidant response element signaling pathway, which controls the expression of genes The object of the present invention are $N^2,N^6$-disubstituted-9-(2-oxacycloalkyl)-9H-purine-2,6-diamine derivatives of the general formula I for use in activation of the whose protein products are involved in the detoxication and elimination of reactive oxidants and electrophilic agents through conjugative reactions and by enhancing cellular antioxidant capacity.

The object of the present invention are $N^2,N^6$-disubstituted-9-(2-oxacycloalkyl)-9H-purine-2,6-diamine derivatives of the general formula I for use as antioxidants for inhibiting lipid, protein and DNA peroxidation in mammals or plants either in vivo or in vitro.

The compounds of the present invention thus can be used as medicaments. They can be used in methods of treatment of a variety of conditions in mammals, especially in humans. In particular, such conditions include skin conditions, such as acne, erythema, redness. The compounds according to the present invention may also be used as antineurodegenerative drugs, or in methods of suppression of immunostimulation (e.g., treatment of arthritis or suppression of transplant rejection).

The compounds according to the present invention show in particular antioxidant, anti-inflammatory, anti-senescent properties.

This invention also provides the compounds of the general formula I for use in the prevention and treatment of many diseases connected with oxidative stress in skin, for example, skin cancer and psoriasis. Oxidative stress and its processes are also necessary for development of fibrosis in fibrotic disorders such as scleroderma, graft versus host disease (GVHD), hypertrophic scars, nephrogenic systemic fibrosis (NSF), and other skin pathologies, e.g. psoriasis, allergic eczema, toxic eczema, atopic dermatitis, lichen planus, hyperpigmentation and herpes simplex lesions, ichthyosis, papilloma, Bowen's disease, seborrheic keratoses, actinic keratoses, basal and squamous cell carcinoma.

The compounds of the present invention can also be used in cosmetics. Cosmetic uses of these compounds and their salts include inhibition, delaying, or reducing the adverse effects of aging and senescence of cells, especially epidermal cells such as keratinocytes or fibroblasts, in vivo and in vitro; the cosmetic uses also include improving the overall appearance and condition of the mammalian skin, in particular human skin, including age-related changes and changes that may not be closely related to aging (e.g., acne, erythema, redness, and the like).

This invention also provides use of the compounds of the general formula I for inhibiting cell senescence and aging in mammals and/or plants, the use comprising application of an effective amount of the $N^2,N^6$-disubstituted-9-(2-oxacycloalkyl)-9H-purine-2,6-diamine derivatives in vivo or in vitro.

This invention also provides use of $N^2,N^6$-disubstituted-9-(2-oxacycloalkyl)-9H-purine-2,6-diamine derivatives for inhibiting or delaying the adverse effects of aging and/or improving the cosmetic appearance of mammalian cells, especially human skin cells, by applying an effective of the $N^2,N^6$-disubstituted-9-(2-oxacycloalkyl)-9H-purine-2,6-diamine derivatives to the mammalian cells.

This invention further provides use of $N^2,N^6$-disubstituted-9-(2-oxacycloalkyl)-9H-purine-2,6-diamine derivatives for rejuvenation of skin cells and/or stimulation of cell proliferation and/or their differentiation in an organism by application of an effective amount of the $N^2,N^6$-disubstituted-9-(2-oxacycloalkyl)-9H-purine-2,6-diamine derivatives of this invention.

As used herein, ameliorating, inhibition and delaying of the adverse effect of aging of mammalian cells means that the development of the morphological changes that normally occur with aging in normal mammalian cells in vitro or in vivo is slowed down, reversed, and/or delayed. The adverse effects of aging also include age-related changes in gene expression and protein biosynthesis. The ameliorative effect referred to herein are those showing increasing the growth rate or total proliferative capacity of the cells treated. Ameliorating, removal or delaying the adverse effects of aging on cells may be detected as a delay or reversal of the onset of age-related morphological and phenotypical changes that normally occur with aging of the cells. Age-related changes in vivo include changes in mammalian tissues, such as the development of, or increase in number or depth of, wrinkles, lines, sagging skin, discolorations, blotchiness, leathery, and/or yellowed appearance associated with the cosmetic appearance of the skin as well as the associated changes in the structural and functional integrity of the tissue.

The $N^2,N^6$-disubstituted-9-(2-oxacycloalkyl)-9H-purine-2,6-diamine derivatives of this invention are effective in improving the overall appearance and condition of the skin, including age-related changes and changes that may not be closely related to aging (e.g., acne, erythema, redness, and the like).

The present invention further provides cosmetic and/or pharmaceutical compositions comprising one or more $N^2,N^6$-disubstituted-9-(2-oxacycloalkyl)-9H-purine-2,6-diamine derivatives of the general formula I, and cosmetically and/or pharmaceutical acceptable carrier.

The $N^2,N^6$-disubstituted-9-(2-oxacycloalkyl)-9H-purine-2,6-diamine derivatives of the general formula I can also be used as cell division and differentiation factors of mammal and human cells.

Pharmaceutical and Cosmetical Compositions

Suitable routes for administration include oral, inhalation, rectal, topical (including dermal, ocular, buccal and sublingual), vaginal and parenteral (including subcutaneous, intramuscular, intravitreous, intravenous, intradermal, intrathecal and epidural) administration. The suitable local administration can be in a form of eye and ear drops and ointments, in the form of vaginal preparations and rectal suppositories. Solutions, creams and ointments are preferred for the treatment of scalp and skin diseases. In cases of eye diseases, an intravitreal injection may be a suitable form of administration. The inhalation dosage forms are suitable in case of lung diseases. A suitable form of prevention of restenosis after vascular or cardiac surgery is the medicated stent. In the case of a gastrointestinal tract disease, oral or rectal administration is preferred. The preferred form of administration depends on the condition of the patient and on the location of the disease. The therapeutic and/or cosmetic compositions comprise from 1% to 95% of the active ingredient. Single-dose forms of administration preferably comprise from 20% to 90% of the active ingredient, and administration forms which are not single-dose preferably comprise from 5% to 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from 0.05 g to 1.0 g of the active ingredient.

The pharmaceutical and cosmetic compositions of the present invention are prepared in a manner known per se, for example by means of conventional mixing, granulating, coating, dissolving or lyophilising processes.

Preferably, solutions of the active ingredient, and in addition also suspensions or dispersions, especially isotonic aqueous solutions, dispersions or suspensions, are used, it being possible for these to be prepared before use, for example in the case of lyophilised compositions which comprise the active substance by itself or together with a carrier, for example mannitol. The pharmaceutical compositions can be sterilized and/or comprise excipients, for example, preservatives, stabilisers, wetting agents and/or emulsifiers, solubilizing agents, salts for regulating the osmotic pressure and/or buffers, and they are prepared in a manner known per se, for example by means of conventional dissolving or lyophilising processes. The solutions or suspensions mentioned can comprise viscosity-increasing substances, such as sodium carboxymethylcellulose, carboxymethylcellulose, dextran, polyvinylpyrrolidone or gelatine.

Suspensions in oil comprise, as the oily component, vegetable, synthetic or semi-synthetic oils customary for injection purposes. Oils which may be mentioned are, in particular, liquid fatty acid esters which contain, as the acid component, a long-chain fatty acid having 8-22, preferably 12-22, carbon atoms (e.g., lauric acid, tridecylic acid, myristic acid, pentadecylic acid, palmitic acid, margaric acid, stearic acid, acid, arachidonic acid, behenic acid, and the like) or corresponding unsaturated acids (e.g., oleic acid, elaidic acid, euric acid, brasidic acid or linoleic acid). Other additional ingredients known in the art can be included if desired (e.g., antioxidants such as vitamin E, β-carotene, or 3,5-di-tert-butyl-4-hydroxytoluene, and the like). The alcohol component of these fatty acid esters generally contains no more than about 6 carbon atoms and can be mono- or polyhydric. Mono-, di-, or trihydric alcohols such as methanol, ethanol, propanol, butanol, or pentanol, or isomers thereof, can be used; glycols and glycerols are generally preferred. Fatty acid esters are preferably, for example, ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris), and/or "Miglyol 812" (triglyceride of saturated fatty acids of chain length C8 to C12 from Hüls AG, Germany), and in particular vegetable oils, such as cottonseed oil, almond oil, olive oil, castor oil, sesame oil, soybean oil and, in particular, groundnut oil as well as mixtures thereof. The preparation of the compositions intended for human use should, of course, be carried out in the customary and approved manner under sterile conditions, and maintained under appropriate conditions up to and including the time of use.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients. Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidone, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidone, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, can also be in the form hard capsules of gelatine or soft, closed capsules of gelatine and a plasticiser, such as glycerol or sorbitol. The hard capsules can contain the active ingredient in the form of granules, mixed for example with fillers, such as maize starch, binders and/or lubricants, such as talc or magnesium stearate, and stabilisers, if appropriate. In soft capsules, the active ingredient is preferably dissolved or suspended in suitable liquid excipients, such as greasy oils, paraffin oil or liquid polyethylene glycol's or fatty acid esters of ethylene glycol or propylene glycol, it being likewise possible to add stabilisers and detergents such as, for example, the polyethylene sorbitan fatty acid ester type.

Other oral forms of administration include, for example, syrups prepared in the customary manner, which comprise the active ingredient, for example, in suspended form and in a concentration of about 5% to 20%, preferably about 10% or in a similar concentration, which results in a suitable individual dose, for example, when 5 or 10 ml are measured out. Other forms include pulverulent or liquid concentrates for preparing shakes, beverages, and the like, e.g. using milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate, stabilizers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example, antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists of, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), preferably sorbitan oleate and/or sorbitan isostearate. Additives to the aqueous phase are, for example, humectants, such as polyalcohols, for example, glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example, hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also can contain emulsifiers and/or additives mentioned in connection with the ointments which increase uptake of water.

Creams are oil-in-water emulsions, which comprise more than 50% of water. Oily bases used are, in particular, fatty alcohols, for example, lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulphates, for example, sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances. Pastes are creams and ointments having secretion-absorbing powder constituents, such as metal oxides, for example, titanium oxide or zinc oxide, and furthermore talc and/or aluminium silicates, which have the task of binding the moisture or secretions present.

Foams (i.e. liquid oil-in-water emulsions packaged in aerosol form) can be administered from pressurised containers. Propellant gases include halogenated hydrocarbons, such as polyhalogenated alkanes such as dichlorofluoromethane and dichlorotetrafluoroethane, or, preferably, non-halogenated gaseous hydrocarbons, air, $N_2O$, or carbon dioxide. The oily phases used are, inter alia, those mentioned above for ointments and creams, and the additives mentioned there are likewise used.

Tinctures and solutions usually comprise an aqueous-ethanolic base to which humectants for reducing evaporation, such as polyalcohols (e.g., glycerol, glycols, polyethylene glycol) and re-oiling substances, such as fatty acid esters with lower polyethylene glycols (e.g., lipophilic substances soluble in the aqueous mixture) to substitute the fatty substances removed from the skin with the ethanol, and, if necessary or desired, other excipients and additives, are admixed. The present invention further provides veterinary compositions comprising at least one active ingredient as above defined together with a veterinary carrier therefor. Veterinary carriers are materials for administering the composition and may be solid, liquid, or gaseous materials, which are inert or acceptable in the veterinary art and are compatible with the active ingredient. These veterinary compositions may be administered orally, parenterally, or by any other desired route.

The present invention also relates to processes or methods of treatment of the disease states mentioned above. The compounds can be administered prophylactically or therapeutically as such or in the form of pharmaceutical compositions, preferably in an amount, which is effective against the diseases mentioned. With a warm-blooded animal, for example, a human requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

BRIEF DESCRIPTION OF DRAWINGS

FIG. 1 shows inhibition of intracellular ROS production by compound 114. The bars show mean±SD. Differences between control cells and cells treated with compound 114 were tested by Student t-test ( $p<0.01$, * $p<0.001$).

EXAMPLES

The following examples serve to illustrate the invention without limiting the scope thereof. Unless otherwise stated, all percentages and the like amounts are based on weight.

The starting materials may be obtained from commercial sources (Sigma, Aldrich, Fluka, etc.) or can be prepared as described below. Thin-layer chromatography was carried out on Silica 60 $F_{254}$ plates (Merck) using $CHCl_3$/MeOH as a developing system and the spots were detected by UV light (254 and 365 nm) and/or 6% (v/v) vanilline in absolute EtOH containing 1% (v/v) of $H_2SO_4$. The column chromatography purification of intermediates was carried out by silica Davisil 40-63 micron (Grace Davision). Elemental analysis was determined using Flash EA 1112 analyzer (Thermo Scientific). The chromatographic purity and molecular mass of prepared compounds was determined using an Alliance 2695 separation module (Waters) linked simultaneously to a DAD detector PDA 996 (Waters) and a Q-Tof micro (Waters) benchtop quadrupole orthogonal acceleration time-of-flight tandem mass spectrometer. Samples were dissolved in DMSO and diluted to a concentration of 10 μg/ml in initial mobile phase (90% 15 mM ammonium formate, pH 4.0 (A)+10% methanol (B)). Samples (10 μl) were injected on a RP-column Symmetry C18 (150 mm×2.1 mm×3.5 μm, Waters) and separated at a flow rate of 0.2 ml/min with the following binary gradient: 0 min, 10% B; 0-24 min, a linear gradient to 90% B, 10 min, followed by 10 min isocratic elution of 90% B. At the end of the gradient, the column was re-equilibrated to initial conditions (15 mM formic acid adjusted to pH 4.0 by ammonium hydroxide was used as solvent (A) and methanol as the organic modifier (solvent B)). The eluent was introduced into the DAD (scanning range 210-400 nm, with 1.2 nm resolution) and an ESI source (source temperature 110° C., capillary voltage +3.0 kV, cone voltage +20 V, desolvation temperature 250° C.). Nitrogen was used both as desolvation gas (500 l/h) as well as cone gas (50 l/h). The data was obtained in positive (ESI+) ionization mode in the 50-1000 m/z range.

$^1H$ and $^{13}C$ NMR spectra were recorded on Jeol ECA-500 operating at a frequency of 500 MHz ($^1H$) and 126 MHz ($^{13}C$) or Bruker Avance operating at a frequency of 300 MHz ($^1H$) and 75 MHz ($^{13}C$), respectively. Samples were prepared by dissolving substances in DMSO-$d_6$ and chemical shifts were calibrated to residual solvent peak (DMSO, 2.49 ppm for proton) and DMSO-$d_6$ (39.5 ppm for carbon).

N$^2$,N$^6$-disubstituted-9-(2-oxacycloalkyl)-9H-purine-2,6-diamine derivatives were prepared in three steps, starting from 2,6-dichloro-9H-purine. Firstly, (2-oxacycloalkyl) substituents were introduced to the N9-position of purine moiety by hydroamination of corresponding α,β-unsaturated O-heterocycles by 2,6-dichloro-9H-purine in ethyl acetate catalyzed by trifluoroacetic acid according to protocol in Szučová et al. 2009 *Bioorg. Med. Chem.* 17, 1938-1947. 2,3,4,5-tetrahydrooxepin was prepared by endo cycloisomeration of 5-hexyn-1-ol catalyzed by tetradentate nitrogen-phosphorous mixed ligand ruthenium complex following methodology published in Liu et al. (2010) *Chem. Eur. J.* 16, 7889-7897 and Mitchell et al. (1973) *J. Chem. Soc., Dalton Trans.* (8), 846-854.

The intermediates were further subjected to the nucleophilic substitution at C6 position with appropriate side-chain amines and triethylamine in refluxing propanol followed by nucleophilic substitution of C2 chlorine atom. Small amines such as methylamine or dimethylamine were introduced to C2 position using a modified protocol published in Kelley et al. (1989) *J. Med. Chem.* 32, 218-224, whereas amines with larger molecular mass were introduced to C2 position according to Kurimoto et al. (2003) *Bioorg. Med. Chem.* 11, 5501-5508.

Modification of Purines at N9-Position

A) Hydroamination of α,β-Unsaturated O-Heterocycles

Example 1
2,6-Dichloro-9-(tetrahydrofuran-2-yl)-9H-purine

To a suspension of 2,6-dichloro-9H-purine (1 eq., 5 g) and 2,3-dihydrofuran (2.5 eq.) under Ar atmosphere in dry ethyl acetate (40 ml) was trifluoroacetic acid (2.5 eq) dropwise added and resulting solution was stirred at room temperature for 2 hours. After cooling in ice bath pH of the reaction mixture was adjusted to 7-8 by conc. NH$_3$/water (2:3, v/v) and the layers were separated. The water phase was re-extracted by ethyl acetate (5×25 ml). Combined organic layers were washed with brine (2×25 ml), dried (Na$_2$SO$_4$) and evaporated under reduced pressure. The product as a pale yellow solid was obtained by crystallization from petroleum ether. Pale yellow solid, chemical formula: C$_9$H$_8$Cl$_2$N$_4$O, yield (%): 98. HPLC-UV/VIS retention time, purity (min., %): 21.07, 99.9. ESI$^+$-MS m/z (rel. int. %, ion): 258.8 (8, [$^{35}$Cl-M+H]$^+$), 260.8 (6, [$^{37}$Cl-M+H]$^+$), 188.8 (100, [$^{35}$Cl-M-THF+H]$^+$), 190.8 (68, [$^{37}$Cl-M-THF+H]$^+$). $^1$H NMR (500 MHz, DMSO-d$_6$) δ (ppm): 2.01-2.08 (m, 1H), 2.11-2.20 (m, 1H), 2.41-2.46 (m, 2H), 3.93 (q, J=7.5 Hz, 1H), 4.18 (td, J=7.9, 5.7 Hz, 1H), 6.33 (dd, J=5.8, 4.3 Hz, 1H), 8.82 (s, 1H). $^{13}$C NMR (126 MHz, DMSO-d$_6$) δ (ppm): 23.8, 31.3, 69.2, 85.6, 131.0, 146.4, 149.6, 150.9, 152.6.

Example 2 2,6-Dichloro-9-(tetrahydro-2H-pyran-2-yl)-9H-purine

To a suspension of 2,6-dichloro-9H-purine (1 eq., 5 g) and 3,4-dihydro-2H-pyran (2 eq.) under Ar atmosphere in dry ethyl acetate (50 ml) was trifluoroacetic acid (1.8 eq.) dropwise added and resulting solution was stirred at room temperature for 2 hours. After cooling in ice bath pH of the reaction mixture was adjusted to 7-8 by conc. NH$_3$/water (2:3, v/v). Resulting solid was filtered, washed with cold water and dried at room temperature. Second portion of product was obtained by extraction of filtrate and washings by ethyl acetate (3×25 ml). The combined organic layers were washed with brine (2×15 ml) dried (Na$_2$SO$_4$) and concentrated under reduced pressure to give a yellow gel. The solid material was obtained after crystallization from diethyl ether. White solid, chemical formula: C$_{10}$H$_{10}$Cl$_2$N$_4$O, yield (%): 88. HPLC-UV/VIS retention time, purity (min., %): 22.87, 98.4. ESI$^+$-MS m/z (rel. int. %, ion): 273.0 (10, [$^{35}$Cl-M+H]$^+$), 275.0 (8, [$^{37}$Cl-M+H]$^+$), 189.0 (100, [$^{35}$Cl-M-THP+H]$^+$), 191.0 (74, [$^{37}$Cl-M-THP+H]$^+$). $^1$H NMR (500 MHz, DMSO-d$_6$) δ (ppm): 1.56-1.61 (m, 2H), 1.73-1.77 (m, 1H), 1.94-2.01 (m, 2H), 2.21-2.29 (m, 1H), 3.70-3.75 (m, 1H), 4.00-4.03 (m, 1H), 5.73 (dd, J=10.9, 2.3 Hz, 1H), 8.95 (s, 1H). $^{13}$C NMR (126 MHz, DMSO-d$_6$) δ (ppm): 22.0, 24.3, 29.6, 67.7, 81.6, 130.5, 146.4, 149.9, 151.2, 152.7.

Substitution of Purines at C6 Position

Synthesis of 2-chloro-6-substituted-9-(2-oxacycloalkyl)-9H-purine Derivatives—Typical Procedure Mixture of 2,6-dichloro-9-(2-oxacycloalkyl)-9H-purine (1 eq., 250 mg), side-chain amine (1.2 eq.) and triethylamine (2.5 eq. and in case of salts 3.5 eq., respectively) were refluxed in propanol (9 ml) for 4 hours. After evaporation under reduced pressure the residue was treated with ice cold water (15 ml).

Method A) If a solid material was obtained—the solid was filtered, washed well with ice cold water and dried.

Method B) If no solid material was obtained—the mixture was extracted by ethyl acetate (5×10 ml). Combined organic layers were washed using brine (2×10 ml), dried (Na$_2$SO$_4$) and concentrated under reduced pressure.

The crude material was purified by silica column chromatography using chloroform/methanol as a mobile phase starting from pure chloroform with methanol gradient.

Example 3 2-Chloro-6-furfurylamino-9-(tetrahydrofuran-2-yl)-9H-purine

Prepared from 2,6-dichloro-9-(tetrahydrofuran-2-yl)-9H-purine and furfurylamine, work-up using A. White solid, chemical formula: C$_{14}$H$_{14}$ClN$_5$O$_2$, yield (%): 85. HPLC-UV/VIS retention time, purity (min., %): 24.43, 99.8. ESI$^+$-MS m/z (rel. int. %, ion): 319.8 (100, [$^{35}$Cl-M+H]$^+$), 321.8 (45, [$^{37}$Cl-M+H]$^+$), 249.8 (83, [$^{35}$Cl-M-THF+H]$^+$), 251.8 (35, [$^{37}$Cl-M-THF+H]$^+$). $^1$H NMR (500 MHz, DMSO-d$_6$) δ (ppm): 1.96-2.04 (m, 1H), 2.11-2.20 (m, 1H), 2.36-2.41 (m, 2H), 3.89 (q, J=7.3 Hz, 1H), 4.11 (td, J=7.8, 5.9 Hz, 1H), 4.61 (d, J=5.5 Hz, 2H), 6.19 (t, J=5.2 Hz, 1H), 6.25 (d, J=2.8 Hz, 1H), 6.37 (bs, 1H), 7.54-7.55 (m, 1H), 8.28 (s, 1H), 8.76 (t, J=5.2 Hz, 1H). $^{13}$C NMR (126 MHz, DMSO-d$_6$) δ (ppm): 24.1, 31.2, 36.6, 68.7, 84.4, 107.1, 110.5, 118.6, 139.7, 142.0, 149.3, 152.0, 152.9, 154.7.

Example 4 2-Chloro-6-[(5-methylfurfuryl)amino]-9-(tetrahydrofuran-2-yl)-9H-purine Prepared from 2,6-dichloro-9-(tetrahydrofuran-2-yl)-9H-purine and 5-methylfurfurylamine, work-up using B. White solid, chemical formula: C$_{15}$H$_{16}$ClN$_5$O$_2$, yield (%): 66. HPLC-UV/VIS retention time, purity (min., %): 26.05, 99.9. ESI$^+$-MS m/z (rel. int. %, ion): 334.6 (100, [$^{35}$Cl-M+H]$^+$), 336.7 (64, [$^{37}$Cl-M+H]$^+$), 264.5 (87, [$^{35}$Cl-M-THF+H]$^+$), 266.6 (43, [$^{37}$Cl-M-THF+H]$^+$). $^1$H NMR (500 MHz, DMSO-d$_6$) δ (ppm): 1.96-2.04 (m, 1H), 2.13-2.17 (m, 1H), 2.20 (s, 3H), 2.36-2.41 (m, 2H), 3.89 (q, J=7.3 Hz, 1H), 4.11 (q, J=7.2 Hz, 1H), 4.55 (d, J=5.5 Hz, 2H), 5.96 (bs, 1H), 6.11 (d, J=2.8 Hz, 1H), 6.19 (t, J=5.2 Hz, 1H), 8.28 (s, 1H), 8.72

(bs, 1H). $^{13}$C NMR (126 MHz, DMSO-d$_6$) δ (ppm): 13.3, 24.1, 31.2, 36.6, 68.7, 84.4, 106.4, 107.9, 118.6, 139.6, 149.3, 150.1, 150.5, 152.9, 154.6.

Example 5 2-Chloro-6-benzylamino-9-(tetrahydrofuran-2-yl)-9H-purine

Prepared from 2,6-dichloro-9-(tetrahydrofuran-2-yl)-9H-purine and benzylamine, work-up using B. White solid, chemical formula: C$_{16}$H$_{16}$ClN$_5$O, yield (%): 65. HPLC-UV/VIS retention time, purity (min., %): 26.39, 99.9. ESI$^+$-MS m/z (rel. int. %, ion): 330.7 (100, [$^{35}$Cl-M+H]$^+$), 332.7 (63, [$^{37}$Cl-M+H]$^+$), 260.5 (82, [$^{35}$Cl-M-THF+H]$^+$), 262.6 (40, [$^{37}$Cl-M-THF+H]$^+$). $^1$H NMR (500 MHz, DMSO-d$_6$) δ (ppm): 1.99-2.04 (m, 1H), 2.13-2.18 (m, 1H), 2.38-2.39 (m, 2H), 3.88-3.90 (m, 1H), 4.10-4.11 (m, 1H), 4.63 (bs, 2H), 6.18-6.19 (m, 1H), 7.22 (bs, 1H), 7.31 (bs, 4H), 8.28 (s, 1H), 8.86 (bs, 1H). $^{13}$C NMR (126 MHz, DMSO-d$_6$) δ (ppm): 24.1, 31.2, 43.1, 68.7, 84.4, 118.5, 126.8, 2×127.2, 2×128.2, 139.2, 139.6, 149.2, 153.0, 154.9.

Example 6 2-Chloro-6-[(3-hydroxybenzyl)amino]-9-(tetrahydrofuran-2-yl)-9H-purine Prepared from 2,6-dichloro-9-(tetrahydrofuran-2-yl)-9H-purine and 3-(aminomethyl)phenol, work-up using A. White solid, chemical formula: C$_{16}$H$_{16}$ClN$_5$O$_2$, yield (%): 94. HPLC-UV/VIS retention time, purity (min., %): 23.33, 99.2. ESI$^+$-MS m/z (rel. int. %, ion): 345.8 (100, [$^{35}$Cl-M+H]$^+$), 347.8 (40, [$^{37}$Cl-M+H]$^+$), 275.8 (83, [$^{35}$Cl-M-THF+H]$^+$), 277.8 (35, [$^{37}$Cl-M-THF+H]$^+$). $^1$H NMR (500 MHz, DMSO-d$_6$) δ (ppm): 1.98-2.03 (m, 1H), 2.14-2.19 (m, 1H), 2.39 (dd, J=12.8, 7.3 Hz, 2H), 3.89 (q, J=7.3 Hz, 1H), 4.11 (dd, J=13.8, 7.6 Hz, 1H), 4.56 (d, J=6.1 Hz, 2H), 6.19 (t, J=5.2 Hz, 1H), 6.60 (dd, J=7.9, 1.5 Hz, 1H), 6.70 (s, 1H), 6.73 (d, J=7.8 Hz, 1H), 7.08 (t, J=7.6 Hz, 1H), 8.28 (s, 1H), 8.81 (t, J=6.1 Hz, 1H), 9.31 (s, 1H). $^{13}$C NMR (126 MHz, DMSO-d$_6$) δ (ppm): 24.1, 31.2, 42.9, 68.7, 84.4, 113.7, 113.8, 117.7, 118.5, 129.2, 139.5, 140.7, 149.2, 153.1, 154.9, 157.3.

Example 7 2-Chloro-6-[(4-hydroxybenzyl)amino]-9-(tetrahydrofuran-2-yl)-9H-purine Prepared from 2,6-dichloro-9-(tetrahydrofuran-2-yl)-9H-purine and 4-(aminomethyl)phenol, work-up using A. White solid, chemical formula: C$_{16}$H$_{16}$ClN$_5$O$_2$, yield (%): 98. HPLC-UV/VIS retention time, purity (min., %): 23.02, 97.6. ESI$^+$-MS m/z (rel. int. %, ion): 345.8 (100, [$^{35}$Cl-M+H]$^+$), 347.8 (45, [$^{37}$Cl-M+H]$^+$), 275.8 (85, [$^{35}$Cl-M-THF+H]$^+$), 277.8 (35, [$^{37}$Cl-M-THF+H]$^+$). $^1$H NMR (500 MHz, DMSO-d$_6$) δ (ppm): 1.96-2.04 (m, 1H), 2.12-2.20 (m, 1H), 2.36-2.41 (m, 2H), 3.89 (q, J=7.3 Hz, 1H), 4.11 (td, J=7.7, 6.2 Hz, 1H), 4.51 (d, J=5.2 Hz, 2H), 6.18 (t, J=5.2 Hz, 1H), 6.68 (d, J=8.6 Hz, 2H), 7.14 (d, J=8.3 Hz, 2H), 8.25 (s, 1H), 8.69 (app. t, 1H), 9.23 (s, 1H). $^{13}$C NMR (126 MHz, DMSO-d$_6$) δ (ppm): 24.0, 31.1, 42.6, 68.6, 84.3, 2×114.9, 118.5, 2×128.6, 129.3, 139.3, 149.1, 153.0, 154.7, 156.2.

Example 8 2-Chloro-6-[(2-methoxybenzyl)amino]-9-(tetrahydrofuran-2-yl)-9H-purine Prepared from 2,6-dichloro-9-(tetrahydrofuran-2-yl)-9H-purine and 2-methoxybenzylamine, work-up using B. White solid, chemical formula: C$_{17}$H$_{18}$ClN$_5$O$_2$, yield (%): 53. HPLC-UV/VIS retention time, purity (min., %): 26.97, 98.7. ESI$^+$-MS m/z (rel. int. %, ion): 360.3 (100, [$^{35}$Cl-M+H]$^+$), 362.3 (65, [$^{37}$Cl-M+H]$^+$), 290.6 (88, [$^{35}$Cl-M-THF+H]$^+$), 292.6 (46, [$^{37}$Cl-M-THF+H]$^+$). $^1$H NMR (500 MHz, DMSO-d$_6$) δ (ppm): 1.99-2.03 (m, 1H), 2.14-2.18 (m, 1H), 2.38-2.42 (m, 2H), 3.82 (s, 3H), 3.89 (q, J=7.3 Hz, 1H), 4.09-4.14 (m, 1H), 4.61 (d, J=6.1 Hz, 2H), 6.19 (t, J=5.0 Hz, 1H), 6.85 (t, J=7.5 Hz, 1H), 6.98 (d, J=7.9 Hz, 1H), 7.10 (d, J=7.3 Hz, 1H), 7.21 (t, J=7.6 Hz, 1H), 8.30 (s, 1H), 8.63 (t, J=6.0 Hz, 1H). $^{13}$C NMR (126 MHz, DMSO-d$_6$) δ (ppm): 24.1, 31.2, 38.4, 55.3, 68.7, 84.4, 110.4, 118.6, 120.1, 126.43, 126.8, 127.9, 139.5, 149.2, 153.1, 155.1, 156.5.

Example 9 2-Chloro-6-[(4-methoxybenzyl)amino]-9-(tetrahydrofuran-2-yl)-9H-purine Prepared from 2,6-dichloro-9-(tetrahydrofuran-2-yl)-9H-purine and 4-methoxybenzylamine, work-up using B. Pale yellow solid, chemical formula: C$_{17}$H$_{18}$ClN$_5$O$_2$, yield (%): 54. HPLC-UV/VIS retention time, purity (min., %): 26.17, 98.3. ESI$^+$-MS m/z (rel. int. %, ion): 360.3 (100, [35Cl-M+H]$^+$), 362.3 (68, [37Cl-M+H]$^+$), 290.6 (87, [$^{35}$Cl-M-THF+H]$^+$), 292.6 (48, [37Cl-M-THF+H]$^+$). $^1$H NMR (500 MHz, DMSO-d$_6$) δ (ppm): 1.97-2.02 (m, 1H), 2.13-2.18 (m, 1H), 2.36-2.40 (m, 2H), 3.70 (s, 3H), 3.88 (q, J=7.4 Hz, 1H), 4.08-4.12 (m, 1H), 4.55 (d, J=6.1 Hz, 2H), 6.18 (t, J=5.2 Hz, 1H), 6.86 (d, J=8.6 Hz, 2H), 7.26 (d, J=8.9 Hz, 2H), 8.27 (s, 1H), 8.79 (t, J=6.0 Hz, 1H). $^{13}$C NMR (126 MHz, DMSO-d$_6$) δ (ppm): 24.1, 31.2, 42.5, 55.0, 68.7, 84.4, 2×113.6, 118.5, 128.4, 128.7, 131.1, 139.5, 149.1, 153.0, 154.7, 158.2.

Example 10 2-Chloro-6-[(4-hydroxy-3-methoxybenzyl)amino]-9-(tetrahydrofuran-2-yl)-9H-purine Prepared from 2,6-dichloro-9-(tetrahydrofuran-2-yl)-9H-purine and 4-(aminomethyl)-2-methoxyphenol hydrochloride, work-up using A. White solid, chemical formula: C$_{17}$H$_{18}$ClN$_5$O$_3$, yield (%): 96. HPLC-UV/VIS retention time, purity (min., %): 23.27, 99.9. ESI$^+$-MS m/z (rel. int. %, ion): 375.8 (99, [$^{35}$Cl-M+H]$^+$), 377.8 (43, [$^{37}$Cl-M+H]$^+$), 305.8 (100, [$^{35}$Cl-M-THF+H]$^+$), 307.8 (42, [$^{37}$Cl-M-THF+H]$^+$). $^1$H NMR (500 MHz, DMSO-d$_6$) δ (ppm): 1.96-2.04 (m, 1H), 2.12-2.20 (m, 1H), 2.36-2.41 (m, 2H), 3.73 (s, 3H), 3.89 (q, J=7.3 Hz, 1H), 4.11 (td, J=7.7, 6.2 Hz, 1H), 4.51 (d, J=5.5 Hz, 2H), 6.18 (t, J=5.2 Hz, 1H), 6.68 (d, J=7.9 Hz, 1H), 6.73 (d, J=7.9 Hz, 1H), 7.00 (s, 1H), 8.25 (s, 1H), 8.68 (app. t, 1H), 8.79 (s, 1H). $^{13}$C NMR (126 MHz, DMSO-d$_6$) δ (ppm): 24.0, 31.1, 43.0, 55.4, 68.6, 84.3, 112.3, 115.1, 118.5, 120.01, 129.9, 139.3, 145.4, 147.2, 149.1, 153.0, 154.7.

Example 11 2-Chloro-6-furfurylamino-9-(tetrahydro-2H-pyran-2-yl)-9H-purine

Prepared from 2,6-dichloro-9-(tetrahydro-2H-pyran-2-yl)-9H-purine and furfurylamine, work-up using A. White solid, chemical formula: C$_{15}$H$_{16}$ClN$_5$O$_2$, yield (%): 83. HPLC-UV/VIS retention time, purity (min., %): 25.57, 99.9. ESI$^+$-MS m/z (rel. int. %, ion): 334.0 (100, [$^{35}$Cl-M+H]$^+$), 336.0 (56, [$^{37}$Cl-M+H]$^+$), 249.9 (92, [$^{35}$Cl-M-THP+H]$^+$), 251.9 (44, [$^{37}$Cl-M-THP+H]$^+$). $^1$H NMR (500 MHz, DMSO-d$_6$) δ (ppm): 1.53-1.58 (m, 2H), 1.68-1.74 (m, 1H), 1.91-1.95 (m, 2H), 2.15-2.23 (m, 1H), 3.65-3.70 (m, 1H), 3.97-3.99 (m, 1H), 4.62 (d, J=4.0 Hz, 2H), 5.55-5.57 (m, 1H), 6.26 (d, J=2.8 Hz, 1H), 6.37 (bs, 1H), 7.55 (d, J=0.9 Hz, 1H), 8.39 (s, 1H), 8.78 (t, J=5.3 Hz, 1H). $^{13}$C NMR (126

MHz, DMSO-$d_6$) δ (ppm): 22.2, 24.4, 29.9, 36.6, 67.6, 80.8, 107.0, 110.4, 118.1, 139.51, 141.9, 149.4, 151.9, 153.1, 154.6.

Example 12 2-Chloro-6-[(5-methylfurfuryl)amino]-9-(tetrahydro-2H-pyran-2-yl)-9H-purine Prepared from 2,6-dichloro-9-(tetrahydro-2H-pyran-2-yl)-9H-purine and 5-methylfurfurylamine, work-up using B. White solid, chemical formula: $C_{16}H_{18}ClN_5O_2$, yield (%): 96. HPLC-UV/VIS retention time, purity (min., %): 26.98, 99.9. ESI$^+$-MS m/z (rel. int. %, ion): 348.8 (100, [$^{35}$Cl-M+H]$^+$), 350.8 (64, [$^{37}$Cl-M+H]$^+$), 264.7 (91, [$^{35}$Cl-M-THP+H]$^+$), 266.7 (47, [$^{37}$Cl-M-THP+H]$^+$). $^1$H NMR (500 MHz, DMSO-$d_6$) δ (ppm): 1.53-1.58 (m, 2H), 1.67-1.76 (m, 1H), 1.91-1.95 (m, 2H), 2.13-2.20 (m, 4H), 3.65-3.70 (m, 1H), 3.98 (dd, J=10.9, 1.7 Hz, 1H), 4.55 (d, J=5.5 Hz, 2H), 5.55-5.57 (m, 1H), 5.96 (bs, 1H), 6.11 (d, J=3.1 Hz, 1H), 8.38 (s, 1H), 8.73 (t, J=5.5 Hz, 1H). $^{13}$C NMR (126 MHz, DMSO-$d_6$) δ (ppm): 13.2, 22.3, 24.4, 29.9, 36.7, 67.6, 80.8, 106.4, 107.9, 118.1, 139.5, 149.4, 150.1, 150.5, 153.1, 154.6.

Example 13 2-Chloro-6-benzylamino-9-(tetrahydro-2H-pyran-2-yl)-9H-purine

Prepared from 2,6-dichloro-9-(tetrahydro-2H-pyran-2-yl)-9H-purine and benzylamine, work-up using A. White solid, chemical formula: $C_{17}H_{18}ClN_5O$, yield (%): 97. HPLC-UV/VIS retention time, purity (min., %): 27.28, 99.9. ESI$^+$-MS m/z (rel. int. %, ion): 344.8 (100, [$^{35}$Cl-M+H]$^+$), 346.8 (64, [$^{37}$Cl-M+H]$^+$), 260.6 (90, [$^{35}$Cl-M-THP+H]$^+$), 262.6 (47, [$^{37}$Cl-M-THP+H]$^+$). $^1$H NMR (500 MHz, DMSO-$d_6$) δ (ppm): 1.53-1.60 (m, 2H), 1.67-1.76 (m, 1H), 1.93 (bs, 2H), 2.16-2.24 (m, 1H), 3.65-3.70 (m, 1H), 3.98 (d, J=11.0 Hz, 1H), 4.64 (d, J=3.7 Hz, 2H), 5.55 (dd, J=11.0, 1.8 Hz, 1H), 7.22 (t, J=6.6 Hz, 1H), 7.28-7.33 (m, 4H), 8.38 (s, 1H), 8.88 (t, J=6.0 Hz, 1H). $^{13}$C NMR (126 MHz, DMSO-$d_6$) δ (ppm): 22.3, 24.4, 29.9, 43.1, 67.6, 80.8, 118.0, 126.8, 2×127.2, 2×128.2, 139.2, 139.4, 149.3, 153.2, 154.9.

Example 14 2-Chloro-6-[(4-methylbenzyl)amino]-9-(tetrahydro-2H-pyran-2-yl)-9H-purine Prepared from 2,6-dichloro-9-(tetrahydro-2H-pyran-2-yl)-9H-purine and 4-methylbenzylamine, work-up using B. White solid, chemical formula: $C_{18}H_{20}ClN_5O$, yield (%): 99. HPLC-UV/VIS retention time, purity (min., %): 28.63, 98.5. ESI$^+$-MS m/z (rel. int. %, ion): 358.8 (100, [$^{35}$Cl-M+H]$^+$), 360.8 (72, [$^{37}$Cl-M+H]$^+$), 274.6 (90, [$^{35}$Cl-M-THP+H]$^+$), 276.6 (59, [$^{37}$Cl-M-THP+H]$^+$). $^1$H NMR (500 MHz, DMSO-$d_6$) δ (ppm): 1.53-1.58 (m, 2H), 1.67-1.76 (m, 1H), 1.90-1.94 (m, 2H), 2.15-2.27 (m, 4H), 3.64-3.70 (m, 1H), 3.98 (d, J=11.3 Hz, 1H), 4.58 (d, J=4.9 Hz, 2H), 5.55 (dd, J=10.9, 2.0 Hz, 1H), 7.10 (d, J=7.6 Hz, 2H), 7.20 (d, J=7.9 Hz, 2H), 8.37 (s, 1H), 8.84 (t, J=6.1 Hz, 1H). $^{13}$C NMR (126 MHz, DMSO-$d_6$) δ (ppm): 20.6, 22.3, 24.5, 29.9, 42.8, 67.6, 80.8, 118.0, 2×127.2, 2×128.8, 135.8, 136.1, 139.4, 149.3, 153.3, 154.9.

Example 15 2-Chloro-6-{[4-(trifluoromethyl)benzyl]amino}-9-(tetrahydro-2H-pyran-2-yl)-9H-purine Prepared from 2,6-dichloro-9-(tetrahydro-2H-pyran-2-yl)-9H-purine and 4-(trifluoromethyl)benzylamine, work-up using A. White solid, chemical formula: $C_{18}H_{17}ClF_3N_5O$, yield (%): 73. HPLC-UV/VIS retention time, purity (min., %): 29.12, 99.9. ESI$^+$-MS m/z (rel. int. %, ion): 412.7 (97, [$^{35}$Cl-M+H]$^+$), 414.7 (65, [$^{37}$Cl-M+H]$^+$), 328.7 (90, [$^{35}$Cl-M-THP+H]), 330.7 (64, [$^{37}$Cl-M-THP+H]$^+$). $^1$H NMR (500 MHz, DMSO-$d_6$) δ (ppm): 1.55 (bs, 2H), 1.67-1.76 (m, 1H), 1.93 (bs, 2H), 2.16-2.24 (m, 1H), 3.65-3.70 (m, 1H), 3.98 (d, J=11.3 Hz, 1H), 4.72 (d, J=5.5 Hz, 2H), 5.55-5.57 (m, 1H), 7.53 (d, J=7.9 Hz, 2H), 7.68 (d, J=8.3 Hz, 2H), 8.41 (s, 1H), 8.98 (t, J=6.0 Hz, 1H). $^{13}$C NMR (126 MHz, DMSO-$d_6$) δ (ppm): 22.3, 24.4, 29.9, 42.8, 67.6, 80.9, 118.1, 124.3 (q, $^1J_{CF}$=272.3 Hz), 2×125.2 (q, $^3J_{CF}$=2.4 Hz), 127.5 (q, $^2J_{CF}$=32.2 Hz), 2×127.8, 139.7, 144.1, 149.4, 153.2, 154.9.

Example 16 2-Chloro-6-[(3-hydroxybenzyl)amino]-9-(tetrahydro-2H-pyran-2-yl)-9H-purine Prepared from 2,6-dichloro-9-(tetrahydro-2H-pyran-2-yl)-9H-purine and 3-(aminomethyl)phenol, work-up using B. White solid, chemical formula: $C_{17}H_{18}ClN_5O_2$, yield (%): 73. HPLC-UV/VIS retention time, purity (min., %): 24.43, 99.8. ESI$^+$-MS m/z (rel. int. %, ion): 359.8 (100, [$^{35}$Cl-M+H]$^+$), 361.8 (40, [$^{37}$Cl-M+H]$^+$), 275.8 (99, [$^{35}$Cl-M-THP+H]$^+$), 277.8 (38, [$^{37}$Cl-M-THP+H]$^+$). $^1$H NMR (500 MHz, DMSO-$d_6$) δ (ppm): 1.53-1.58 (m, 2H), 1.70-1.74 (m, 1H), 1.90-1.95 (m, 2H), 2.16-2.21 (m, 1H), 3.65-3.70 (m, 1H), 3.96-3.99 (m, 1H), 4.56 (d, J=6.1 Hz, 2H), 5.56 (dd, J=11.0, 2.1 Hz, 1H), 6.60 (dd, J=7.9, 1.8 Hz, 1H), 6.70 (s, 1H), 6.73 (d, J=7.9 Hz, 1H), 7.08 (t, J=7.8 Hz, 1H), 8.38 (s, 1H), 8.83 (t, J=6.3 Hz, 1H), 9.31 (s, 1H). $^{13}$C NMR (126 MHz, DMSO-$d_6$) δ (ppm): 22.3, 24.5, 29.9, 42.9, 67.7, 80.9, 113.7, 113.8, 117.7, 118.06, 129.2, 139.4, 140.6, 149.3, 153.3, 154.9, 157.3.

Example 17 2-Chloro-6-[(3-hydroxybenzyl)amino]-9-(tetrahydro-2H-pyran-2-yl)-9H-purine Prepared from 2,6-dichloro-9-(tetrahydro-2H-pyran-2-yl)-9H-purine and 4-(aminomethyl)phenol, work-up using B. White solid, chemical formula: $C_{17}H_{18}ClN_5O_2$, yield (%): 99. HPLC-UV/VIS retention time, purity (min., %): 23.98, 98.0. ESI$^+$-MS m/z (rel. int. %, ion): 360.8 (90, [$^{35}$Cl-M+H]$^+$), 362.8 (51, [$^{37}$Cl-M+H]$^+$), 276.7 (100, [$^{35}$Cl-M-THP+H]$^+$), 278.6 (58, [$^{37}$Cl-M-THP+H]$^+$). $^1$H NMR (500 MHz, DMSO-$d_6$) δ (ppm): 1.53-1.57 (m, 2H), 1.67-1.76 (m, 1H), 1.90-1.94 (m, 2H), 2.15-2.23 (m, 1H), 3.64-3.70 (m, 1H), 3.98 (d, J=11.3 Hz, 1H), 4.51 (d, J=5.8 Hz, 2H), 5.55 (d, J=10.7 Hz, 1H), 6.68 (d, J=7.9 Hz, 2H), 7.13 (d, J=8.3 Hz, 2H), 8.36 (s, 1H), 8.76 (t, J=6.1 Hz, 1H), 9.27 (s, 1H). $^{13}$C NMR (126 MHz, DMSO-$d_6$) δ (ppm): 22.3, 24.4, 29.9, 42.6, 67.6, 80.8, 2×115.0, 118.0, 128.5, 128.7, 129.3, 139.3, 149.2, 153.3, 154.8, 156.3.

Example 18 2-Chloro-6-[(4-methoxybenzyl)amino]-9-(tetrahydro-2H-pyran-2-yl)-9H-purine Prepared from 2,6-dichloro-9-(tetrahydro-2H-pyran-2-yl)-9H-purine and 4-methoxybenzylamine, work-up using B. White solid, chemical formula: $C_{18}H_{20}ClN_5O_2$, yield (%): 99. HPLC-UV/VIS retention time, purity (min., %): 27.10, 99.9. ESI$^+$-MS m/z (rel. int. %, ion): 374.8 (98, [$^{35}$Cl-M+H]$^+$), 376.8 (65, [$^{37}$Cl-M+H]$^+$), 290.7 (100, [$^{35}$Cl-M-THP+H]$^+$), 292.7 (62, [$^{37}$Cl-M-THP+H]$^+$). $^1$H NMR (500 MHz, DMSO-$d_6$) δ (ppm): 1.53-1.60 (m, 2H), 1.67-1.76 (m, 1H), 1.90-1.95 (m, 2H), 2.15-2.23 (m, 1H), 3.64-3.67 (m, 1H), 3.70 (s, 3H), 3.98 (dd, J=10.9, 1.7 Hz, 1H), 4.55 (d, J=4.6 Hz, 2H), 5.55 (dd, J=10.9, 1.7 Hz, 1H), 6.86 (d, J=8.6 Hz, 2H), 7.26 (d, J=8.9 Hz, 2H), 8.37 (s, 1H), 8.82 (t, J=6.1 Hz, 1H). $^{13}$C NMR (126 MHz, DMSO-$d_6$) δ (ppm):

22.3, 24.4, 29.9, 42.6, 55.0, 67.6, 80.8, 2×113.6, 118.0, 128.4, 128.7, 131.1, 139.4, 149.2, 153.2, 154.8, 158.2.

Substitution of Purines at C2 Position:

A) Substitution with Primary and Secondary Alkylamines—Typical Procedure

A mixture of 2-chloro-6-substituted-9-(2-oxacycloalkyl)-9H-purine (150 mg, 1 eq.) and amine (20 eq.) was heated at 95° C. under Ar atmosphere in ACE pressure tube for 16 hours. The reaction mixture was evaporated under reduced pressure and the residue was treated with ice cold water (5 ml). The resulting solid was filtered, washed with ice cold water and dried at ambient temperature. The crude material was purified by silica column chromatography using chloroform/methanol as a mobile phase starting from pure chloroform with methanol gradient.

Example 19 2-(Methylamino)-6-furfurylamino-9-(tetrahydrofuran-2-yl)-9H-purine Prepared from 2-chloro-6-furfurylamino-9-(tetrahydrofuran-2-yl)-9H-purine and 8M solution of methylamine in absolute ethanol. White solid, chemical formula: $C_{15}H_{18}N_6O_2$, yield (%): 74. HPLC-UV/VIS retention time, purity (min., %): 22.03, 99.8. ESI$^+$-MS m/z (rel. int. %, ion): 315.0 (100, [M+H]$^+$). $^1$H NMR (500 MHz, DMSO-d$_6$) δ (ppm): 1.93-2.01 (m, 1H), 2.18-2.26 (m, 1H), 2.29-2.36 (m, 1H), 2.41 (bs, 1H), 2.76 (d, J=4.9 Hz, 3H), 3.85 (q, J=7.5 Hz, 1H), 4.10 (q, J=7.2 Hz, 1H), 4.60 (bs, 2H), 6.07 (dd, J=6.7, 3.7 Hz, 1H), 6.22 (d, J=2.8 Hz, 1H), 6.34 (m, 2H), 7.51 (s, 1H), 7.67 (bs, 1H), 7.81 (s, 1H). $^{13}$C NMR (126 MHz, DMSO-d$_6$) δ (ppm): 24.5, 28.1, 30.7, 36.6, 68.3, 83.6, 106.5, 110.3, 113.5, 135.55, 141.5, 150.8, 153.4, 154.2, 159.7.

Example 20 2-(Dimethylamino)-6-furfurylamino-9-(tetrahydrofuran-2-yl)-9H-purine Prepared from 2-chloro-6-furfurylamino-9-(tetrahydrofuran-2-yl)-9H-purine and 5.6M solution of dimethylamine in absolute ethanol. White solid, chemical formula: $C_{16}H_{20}N_6O_2$, yield (%): 97. HPLC-UV/VIS retention time, purity (min., %): 27.07, 99.3. ESI$^+$-MS m/z (rel. int. %, ion): 328.8 (100, [M+H]$^+$), 258.8 ([M-THF+H]$^+$). $^1$H NMR (500 MHz, DMSO-d$_6$) δ (ppm): 1.94-2.01 (m, 1H), 2.21-2.27 (m, 1H), 2.30-2.37 (m, 1H), 2.43-2.48 (m, 1H), 3.06 (s, 6H), 3.84-3.88 (m, 1H), 4.10 (q, J=7.3 Hz, 1H), 4.59 (bs, 2H), 6.09 (dd, J=7.3, 4.0 Hz, 1H), 6.21 (d, J=2.8 Hz, 1H), 6.34 (dd, J=3.1, 1.8 Hz, 1H), 7.51 (d, J=1.2 Hz, 1H), 7.79 (bs, 1H), 7.83 (s, 1H). $^{13}$C NMR (126 MHz, DMSO-d$_6$) δ (ppm): 24.7, 30.5, 36.3, 2×36.9, 68.5, 83.8, 106.5, 110.4, 113.1, 136.27, 141.6, 150.8, 153.5, 153.7, 159.0.

Example 21 2-(Dimethylamino)-6-[(5-methylfurfuryl)amino]-9-(tetrahydrofuran-2-yl)-9H-purine Prepared from 2-chloro-6-[(5-methylfurfuryl)amino]-9-(tetrahydrofuran-2-yl)-9H-purine and 5.6M solution of dimethylamine in absolute ethanol. White solid, chemical formula: $C_{17}H_{22}N_6O_2$, yield (%): 66. HPLC-UV/VIS retention time, purity (min., %): 28.55, 99.9. ESI$^+$-MS m/z (rel. int. %, ion): 343.7 (100, [M+H]$^+$), 273.6 (70, [M-THP+H]$^+$). $^1$H NMR (500 MHz, DMSO-d$_6$) δ (ppm): 1.94-2.00 (m, 1H), 2.19 (s, 3H), 2.22-2.27 (m, 1H), 2.30-2.37 (m, 1H), 2.43-2.47 (m, 1H), 3.07 (s, 6H), 3.86 (dd, J=13.4, 7.6 Hz, 1H), 4.10 (q, J=7.3 Hz, 1H), 4.52 (bs, 2H), 5.93 (d, J=1.8 Hz, 1H), 6.07-6.10 (m, 2H), 7.71 (bs, 1H), 7.82 (s, 1H). $^{13}$C NMR (126 MHz, DMSO-d$_6$) δ (ppm): 13.3, 24.7, 30.5, 36.3, 2×36.9, 68.5, 83.8, 106.3, 107.3, 113.1, 136.2, 150.0, 150.7, 151.6, 153.6, 159.0.

Example 22 2-(Methylamino)-6-benzylamino-9-(tetrahydrofuran-2-yl)-9H-purine

Prepared from 2-chloro-6-benzylamino-9-(tetrahydrofuran-2-yl)-9H-purine and 8M solution of methylamine in absolute ethanol. White solid, chemical formula: $C_{17}H_{20}N_6O$, yield (%): 58. HPLC-UV/VIS retention time, purity (min., %): 24.14, 99.9. ESI$^+$-MS m/z (rel. int. %, ion): 325.7 (100, [M+H]$^+$), 255.6 (38, [M-THF+H]$^+$). $^1$H NMR (500 MHz, DMSO-d$_6$) δ (ppm): 1.93-2.01 (m, 1H), 2.19-2.26 (m, 1H), 2.30-2.36 (m, 1H), 2.42 (bs, 1H), 2.73 (d, J=4.9 Hz, 3H), 3.85 (dd, J=13.9, 7.5 Hz, 1H), 4.10 (q, J=7.3 Hz, 1H), 4.61 (bs, 2H), 6.07 (dd, J=6.6, 3.8 Hz, 1H), 6.31 (bs, 1H), 7.18 (t, J=7.2 Hz, 1H), 7.27 (t, J=7.6 Hz, 2H), 7.33 (d, J=7.6 Hz, 2H), 7.80 (s, 2H). $^{13}$C NMR (126 MHz, DMSO-d$_6$) δ (ppm): 24.6, 28.2, 30.7, 42.6, 68.4, 83.6, 113.5, 126.4, 2×127.3, 2×128.0, 135.5, 140.7, 150.6, 154.4, 159.8.

Example 23 2-(Dimethylamino)-6-benzylamino-9-(tetrahydrofuran-2-yl)-9H-purine Prepared from 2-chloro-6-benzylamino-9-(tetrahydrofuran-2-yl)-9H-purine and 5.6M solution of dimethylamine in absolute ethanol. White solid, chemical formula: $C_{18}H_{22}N_6O$, yield (%): 74. HPLC-UV/VIS retention time, purity (min., %): 28.60, 99.9. ESI$^+$-MS m/z (rel. int. %, ion): 339.7 (100, [M+H]$^+$), 269.6 (73, [M-THF+H]$^+$). $^1$H NMR (500 MHz, DMSO-d$_6$) δ (ppm): 1.94-1.99 (m, 1H), 2.21-2.26 (m, 1H), 2.29-2.36 (m, 1H), 2.43-2.48 (m, 1H), 3.03 (s, 6H), 3.84-3.88 (m, 1H), 4.10 (q, J=7.3 Hz, 1H), 4.59 (bs, 2H), 6.08 (dd, J=7.3, 4.0 Hz, 1H), 7.18 (t, J=7.3 Hz, 1H), 7.26 (t, J=7.6 Hz, 2H), 7.35 (d, J=7.6 Hz, 2H), 7.82 (s, 1H), 7.97 (bs, 1H). $^{13}$C NMR (126 MHz, DMSO-d$_6$) δ (ppm): 24.7, 30.5, 2×36.9, 43.0, 68.5, 83.8, 113.1, 126.4, 2×127.4, 2×128.0, 136.1, 140.8, 150.6, 153.9, 159.0.

Example 24 2-(Dimethylamino)-6-(3-hydroxybenzylamino)-9-(tetrahydrofuran-2-yl)-9H-purine Prepared from 2-chloro-6-(3-hydroxybenzylamino)-9-(tetrahydrofuran-2-yl)-9H-purine and 5.6M solution of dimethylamine in absolute ethanol. White solid, chemical formula: $C_{18}H_{22}N_6O_2$, yield (%): 53. HPLC-UV/VIS retention time, purity (min., %): 25.73, 98.0. ESI$^+$-MS m/z (rel. int. %, ion): 354.8 (100, [M+H]$^+$), 284.8 (53, [M-THF+H]$^+$). $^1$H NMR (500 MHz, DMSO-d$_6$) δ (ppm): 1.94-1.99 (m, 1H), 2.21-2.27 (m, 1H), 2.30-2.37 (m, 1H), 2.43-2.47 (m, 1H), 3.03 (s, 6H), 3.86 (q, J=6.9 Hz, 1H), 4.10 (q, J=7.2 Hz, 1H), 4.52 (bs, 2H), 6.09 (dd, J=7.0, 4.0 Hz, 1H), 6.56 (d, J=8.3 Hz, 1H), 6.75 (s, 1H), 6.76 (s, 1H), 7.05 (t, J=7.8 Hz, 1H), 7.82 (s, 1H), 7.89 (bs, 1H), 9.24 (s, 1H). $^{13}$C NMR (126 MHz, DMSO-d$_6$) δ (ppm): 24.8, 30.5, 2×36.9, 42.9, 68.5, 83.8, 113.1, 113.4, 114.1, 118.02, 129.0, 136.1, 142.2, 150.6, 153.9, 157.2, 159.0.

Example 25 2-(Dimethylamino)-6-[(4-hydroxybenzyl)amino]-9-(tetrahydrofuran-2-yl)-9H-purine Prepared from 2-chloro-6-[(4-hydroxybenzyl)amino]-9-(tetrahydrofuran-2-yl)-9H-purine and 5.6M solution of dimethylamine in absolute ethanol. White solid, chemical formula: $C_{18}H_{22}N_6O_2$, yield (%): 77. HPLC-UV/VIS retention time, purity (min., %): 25.50, 99.07. ESI$^+$-MS m/z (rel. int.

%, ion): 354.8 (100, [M+H]$^+$), 284.8 (54, [M-THF+H]$^+$). $^1$H NMR (500 MHz, DMSO-d$_6$) δ (ppm): 1.94-2.00 (m, 1H), 2.21-2.26 (m, 1H), 2.29-2.37 (m, 1H), 2.44-2.48 (m, 1H), 3.06 (s, 6H), 3.86 (td, J=7.6, 5.8 Hz, 1H), 4.10 (q, J=7.2 Hz, 1H), 4.49 (bs, 2H), 6.08 (dd, J=7.2, 3.8 Hz, 1H), 6.65 (d, J=8.6 Hz, 2H), 7.16 (d, J=8.3 Hz, 2H), 7.73 (bs, 1H), 7.79 (s, 1H), 9.16 (s, 1H). $^{13}$C NMR (126 MHz, DMSO-d$_6$) δ (ppm): 24.6, 30.5, 2×36.9, 42.4, 68.4, 83.7, 113.0, 2×114.7, 2×128.6, 130.9, 135.9, 150.5, 153.8, 155.9, 159.0.

Example 26 2-(Methylamino)-6-[(2-methoxybenzyl)amino]-9-(tetrahydrofuran-2-yl)-9H-purine Prepared from 2-chloro-6-[(2-methoxybenzyl)amino]-9-(tetrahydrofuran-2-yl)-9H-purine and 8M solution of methylamine in absolute ethanol. White solid, chemical formula: C$_{18}$H$_{22}$N$_6$O$_2$, yield (%): 77. HPLC-UV/VIS retention time, purity (min., %): 24.62, 99.0. ESI$^+$-MS m/z (rel. int. %, ion): 355.8 (100, [M+H]$^+$), 285.8 (20, [M-THF+H]$^+$). $^1$H NMR (500 MHz, DMSO-d$_6$) δ (ppm): 1.95-2.00 (m, 1H), 2.22-2.26 (m, 1H), 2.31-2.37 (m, 1H), 2.44 (bs, 1H), 2.70 (d, J=4.3 Hz, 3H), 3.81 (s, 3H), 3.84-3.88 (m, 1H), 4.11 (q, J=7.1 Hz, 1H), 4.59 (bs, 2H), 6.08 (dd, J=6.9, 3.8 Hz, 1H), 6.29 (d, J=3.7 Hz, 1H), 6.83 (t, J=7.3 Hz, 1H), 6.95 (d, J=8.3 Hz, 1H), 7.13 (d, J=7.3 Hz, 1H), 7.16-7.19 (m, 1H), 7.49 (bs, 1H), 7.81 (s, 1H). $^{13}$C NMR (126 MHz, DMSO-d$_6$) δ (ppm): 24.6, 28.1, 30.7, 37.8, 55.2, 68.4, 83.6, 110.1, 113.6, 119.9, 126.9, 127.5, 127.8, 135.5, 150.5, 154.7, 156.5, 159.8.

Example 27 2-(Dimethylamino)-6-[(2-methoxybenzyl)amino]-9-(tetrahydrofuran-2-yl)-9H-purine Prepared from 2-chloro-6-[(2-methoxybenzyl)amino]-9-(tetrahydrofuran-2-yl)-9H-purine and 5.6M solution of dimethylamine in absolute ethanol. White solid, chemical formula: C$_{19}$H$_{24}$N$_6$O$_2$, yield (%): 80. HPLC-UV/VIS retention time, purity (min., %): 28.95, 99.9. ESI$^+$-MS m/z (rel. int. %, ion): 369.8 (100, [M+H]$^+$), 299.8 (63, [M-THF+H]$^+$). $^1$H NMR (500 MHz, DMSO-d$_6$) δ (ppm): 1.94-2.01 (m, 1H), 2.21-2.28 (m, 1H), 2.30-2.37 (m, 1H), 2.44-2.47 (m, 1H), 3.00 (s, 6H), 3.81 (s, 3H), 3.84-3.88 (m, 1H), 4.10 (q, J=7.2 Hz, 1H), 4.61 (bs, 2H), 6.09 (dd, J=7.3, 4.0 Hz, 1H), 6.83 (t, J=7.3 Hz, 1H), 6.95 (d, J=7.9 Hz, 1H), 7.16-7.19 (m, 2H), 7.60 (bs, 1H), 7.82 (s, 1H). $^{13}$C NMR (126 MHz, DMSO-d$_6$) δ (ppm): 24.7, 30.5, 2×36.8, 37.7, 55.2, 68.5, 83.8, 110.2, 113.1, 119.9, 2×127.5, 127.9, 136.1, 150.6, 154.1, 156.5, 159.0.

Example 28 2-(Methylamino)-6-[(4-methoxybenzyl)amino]-9-(tetrahydrofuran-2-yl)-9H-purine Prepared from 2-chloro-6-[(4-methoxybenzyl)amino]-9-(tetrahydrofuran-2-yl)-9H-purine and 8M solution of methylamine in absolute ethanol. White solid, chemical formula: C$_{18}$H$_{22}$N$_6$O$_2$, yield (%): 73. HPLC-UV/VIS retention time, purity (min., %): 23.85, 98.4. ESI$^+$-MS m/z (rel. int. %, ion): 355.8 (100, [M+H]$^+$), 285.8 (20, [M-THF+H]$^+$). $^1$H NMR (500 MHz, DMSO-d$_6$) δ (ppm): 1.93-2.01 (m, 1H), 2.18-2.25 (m, 1H), 2.29-2.36 (m, 1H), 2.41 (bs, 1H), 2.75 (d, J=4.6 Hz, 3H), 3.69 (s, 3H), 3.83-3.87 (m, 1H), 4.10 (q, J=7.2 Hz, 1H), 4.52 (bs, 2H), 6.06 (dd, J=7.0, 4.0 Hz, 1H), 6.30 (d, J=8.6 Hz, 2H), 6.83 (d, J=8.6 Hz, 2H), 7.27 (d, J=8.6 Hz, 2H), 7.74 (bs, 1H), 7.79 (s, 1H). $^{13}$C NMR (126 MHz, DMSO-d$_6$) δ (ppm): 24.6, 28.2, 30.7, 42.0, 54.9, 68.4, 83.6, 3×113.4, 2×128.7, 132.6, 135.4, 150.6, 154.3, 157.9, 159.8.

Example 29 2-(Dimethylamino)-6-[(4-methoxybenzyl)amino]-9-(tetrahydrofuran-2-yl)-9H-purine Prepared from 2-chloro-6-[(4-methoxybenzyl)amino]-9-(tetrahydrofuran-2-yl)-9H-purine and 5.6M solution of dimethylamine in absolute ethanol. White solid, chemical formula: C$_{19}$H$_{24}$N$_6$O$_2$, yield (%): 81. HPLC-UV/VIS retention time, purity (min., %): 28.33, 99.9. ESI$^+$-MS m/z (rel. int. %, ion): 369.8 (100, [M+H]$^+$), 299.8 (74, [M-THF+H]$^+$). $^1$H NMR (500 MHz, DMSO-d$_6$) δ (ppm): 1.94-1.99 (m, 1H), 2.20-2.26 (m, 1H), 2.29-2.36 (m, 1H), 2.43-2.47 (m, 1H), 3.05 (s, 6H), 3.68 (s, 3H), 3.85 (td, J=7.6, 5.8 Hz, 1H), 4.10 (q, J=7.2 Hz, 1H), 4.52 (bs, 2H), 6.08 (dd, J=7.2, 3.8 Hz, 1H), 6.83 (d, J=8.9 Hz, 2H), 7.28 (d, J=8.6 Hz, 2H), 7.81 (s, 1H), 7.87 (bs, 1H). $^{13}$C NMR (126 MHz, DMSO-d$_6$) δ (ppm): 24.7, 30.5, 2×36.9, 42.4, 55.1, 68.5, 83.8, 113.1, 2×113.4, 2×128.7, 132.7, 136.0, 150.5, 153.8, 157.9, 159.0.

Example 30 2-(Dimethylamino)-6-[(4-hydroxy-3-methoxybenzyl)amino]-9-(tetrahydrofuran-2-yl)-9H-purine Prepared from 2-chloro-6-[(4-hydroxy-3-methoxybenzyl)amino]-9-(tetrahydrofuran-2-yl)-9H-purine and 5.6M solution of dimethylamine in absolute ethanol. White solid, chemical formula: C$_{19}$H$_{24}$N$_6$O$_3$, yield (%): 68. HPLC-UV/VIS retention time, purity (min., %): 25.52, 99.7. ESI$^+$-MS m/z (rel. int. %, ion): 384.8 (100, [M+H]$^+$), 314.8 (46, [M-THF+H]$^+$). $^1$H NMR (500 MHz, DMSO-d$_6$) δ (ppm): 1.94-2.01 (m, 1H), 2.19-2.27 (m, 1H), 2.30-2.37 (m, 1H), 2.44-2.47 (m, 1H), 3.07 (s, 6H), 3.71 (s, 3H), 3.86 (td, J=7.7, 5.7 Hz, 1H), 4.10 (q, J=7.3 Hz, 1H), 4.50 (bs, 2H), 6.08 (dd, J=7.0, 4.0 Hz, 1H), 6.66 (d, J=7.9 Hz, 1H), 6.76 (dd, J=7.9, 1.8 Hz, 1H), 6.99 (d, J=1.8 Hz, 1H), 7.73 (bs, 1H), 7.80 (s, 1H), 8.71 (s, 1H). $^{13}$C NMR (126 MHz, DMSO-d$_6$) δ (ppm): 24.7, 30.5, 2×36.9, 42.8, 55.4, 68.4, 83.7, 112.2, 113.0, 115.0, 120.0, 131.5, 135.9, 145.1, 147.1, 150.5, 153.8, 159.0.

Example 31 2-(Methylamino)-6-furfurylamino-9-(tetrahydro-2H-pyran-2-yl)-9H-purine Prepared from 2-chloro-6-furfurylamino-9-(tetrahydro-2H-pyran-2-yl)-9H-purine and 8M solution of methylamine in absolute ethanol. White solid, chemical formula: C$_{16}$H$_{20}$N$_6$O$_2$, yield (%): 52. HPLC-UV/VIS retention time, purity (min., %): 23.42, 99.9. ESI$^+$-MS m/z (rel. int. %, ion): 328.9 (100, [M+H]$^+$), 244.9 (28, [M-THP+H]$^+$). $^1$H NMR (500 MHz, DMSO-d$_6$) δ (ppm): 1.52-1.60 (m, 2H), 1.63-1.72 (m, 1H), 1.84-1.87 (m, 1H), 1.92-1.94 (m, 1H), 2.12-2.20 (m, 1H), 2.78 (d, J=4.9 Hz, 3H), 3.57-3.62 (m, 1H), 3.96-3.99 (m, 1H), 4.63 (bs, 2H), 5.43 (d, J=9.5 Hz, 1H), 6.22 (d, J=3.1 Hz, 1H), 6.34 (m, 2H), 7.51 (d, J=0.9 Hz, 1H), 7.62 (bs, 1H), 7.87 (s, 1H). $^{13}$C NMR (126 MHz, DMSO-d$_6$) δ (ppm): 22.5, 24.5, 28.2, 30.1, 36.3, 67.5, 80.2, 106.5, 110.3, 112.9, 134.9, 141.5, 150.9, 153.4, 154.2, 159.8.

Example 32 2-(Dimethylamino)-6-furfurylamino-9-(tetrahydro-2H-pyran-2-yl)-9H-purine Prepared from 2-chloro-6-furfurylamino-9-(tetrahydro-2H-pyran-2-yl)-9H-purine and 5.6M solution of dimethylamine in absolute ethanol. White solid, chemical formula: C$_{17}$H$_{22}$N$_6$O$_2$, yield (%): 96. HPLC-UV/VIS retention time, purity (min., %): 28.07, 99.9. ESI$^+$-MS m/z (rel. int. %, ion): 343.0 (100, [M+H]$^+$), 258.9 (88, [M-THP+H]$^+$). $^1$H NMR (500 MHz, DMSO-d$_6$) δ (ppm): 1.52-1.56 (m, 2H), 1.66-

1.70 (m, 1H), 1.83-1.86 (m, 1H), 1.91-1.94 (m, 1H), 2.19 (ddd, J=23.9, 12.6, 4.1 Hz, 1H), 3.07 (s, 6H), 3.58-3.64 (m, 1H), 3.97 (dd, J=10.9, 2.0 Hz, 1H), 4.59 (bs, 2H), 5.45 (dd, J=11.0, 2.1 Hz, 1H), 6.21 (d, J=3.4 Hz, 1H), 6.34 (dd, J=3.2, 2.0 Hz, 1H), 7.51 (d, J=1.2 Hz, 1H), 7.79 (bs, 1H), 7.90 (s, 1H). $^{13}$C NMR (75 MHz, DMSO-d$_6$) δ (ppm): 22.6, 24.6, 30.1, 36.4, 2×36.9, 67.5, 80.2, 106.4, 110.3, 112.4, 135.4, 141.5, 150.9, 153.5, 153.7, 159.1.

Example 33 2-(Methylamino)-6-[(5-methylfurfuryl)amino]-9-(tetrahydro-2H-pyran-2-yl)-9H-purine Prepared from 2-chloro-6-[(5-methylfurfuryl)amino]-9-(tetrahydro-2H-pyran-2-yl)-9H-purine and 8M solution of methylamine in absolute ethanol. Pale yellow solid, chemical formula: $C_{17}H_{22}N_6O_2$, yield (%): 79. HPLC-UV/VIS retention time, purity (min., %): 24.98, 99.9. ESI$^+$-MS m/z (rel. int. %, ion): 343.8 (100, [M+H]$^+$), 259.7 (32, [M-THP+H]$^+$). $^1$H NMR (500 MHz, DMSO-d$_6$) δ (ppm): 1.52-1.59 (m, 2H), 1.65-1.69 (m, 1H), 1.83-1.86 (m, 1H), 1.91-1.94 (m, 1H), 2.12-2.18 (m, 1H), 2.19 (s, 3H), 2.77 (d, J=4.6 Hz, 3H), 3.57-3.62 (m, 1H), 3.97 (dd, J=10.9, 2.0 Hz, 1H), 4.54 (bs, 2H), 5.42 (d, J=10.1 Hz, 1H), 5.93 (d, J=1.8 Hz, 1H), 6.08 (d, J=2.8 Hz, 1H), 6.37 (bs, 1H), 7.61 (vbs, 1H), 7.88 (s, 1H). $^{13}$C NMR (126 MHz, DMSO-d$_6$) δ (ppm): 13.3, 22.6, 24.6, 28.2, 30.2, 36.2, 67.6, 80.1, 106.3, 107.4, 112.9, 134.9, 150.1, 150.8, 151.5, 154.1, 159.8.

Example 34 2-(Dimethylamino)-6-[(5-methylfurfuryl)amino]-9-(tetrahydro-2H-pyran-2-yl)-9H-purine Prepared from 2-chloro-6-[(5-methylfurfuryl)amino]-9-(tetrahydro-2H-pyran-2-yl)-9H-purine and 5.6M solution of dimethylamine in absolute ethanol. Pale yellow solid, chemical formula: $C_{18}H_{24}N_6O_2$, yield (%): 86. HPLC-UV/VIS retention time, purity (min., %): 28.90, 99.9. ESI$^+$-MS m/z (rel. int. %, ion): 357.8 (100, [M+H]$^+$), 273.7 (20, [M-THP+H]$^+$). $^1$H NMR (500 MHz, DMSO-d$_6$) δ (ppm): 1.52-1.56 (m, 2H), 1.64-1.72 (m, 1H), 1.83-1.86 (m, 1H), 1.91-1.94 (m, 1H), 2.15-2.18 (m, 1H), 2.19 (s, 3H), 3.08 (s, 6H), 3.58-3.63 (m, 1H), 3.97 (dd, J=11.0, 1.8 Hz, 1H), 4.53 (bs, 2H), 5.45 (dd, J=11.0, 2.1 Hz, 1H), 5.93 (dd, J=2.9, 0.8 Hz, 1H), 6.08 (d, J=2.8 Hz, 1H), 7.71 (bs, 1H), 7.90 (s, 1H). $^{13}$C NMR (126 MHz, DMSO-d$_6$) δ (ppm): 13.2, 22.6, 24.6, 30.1, 36.3, 2×36.9, 67.5, 80.2, 106.3, 107.3, 112.4, 135.4, 150.0, 150.7, 151.6, 153.6, 159.1.

Example 35 2-(Dimethylamino)-6-benzylamino-9-(tetrahydro-2H-pyran-2-yl)-9H-purine Prepared from 2-chloro-6-[(3-hydroxybenzyl)amino]-9-(tetrahydro-2H-pyran-2-yl)-9H-purine and 5.6M solution of dimethylamine in absolute ethanol. White solid, chemical formula: $C_{19}H_{24}N_6O$, yield (%): 86. HPLC-UV/VIS retention time, purity (min., %): 29.12, 99.9. ESI$^+$-MS m/z (rel. int. %, ion): 353.8 (100, [M+H]$^+$), 269.7 (78, [M-THP+H]$^+$). $^1$H NMR (500 MHz, DMSO-d$_6$) δ (ppm): 1.51-1.57 (m, 2H), 1.63-1.72 (m, 1H), 1.83-1.86 (m, 1H), 1.91-1.94 (m, 1H), 2.19 (ddd, J=24.0, 12.5, 3.7 Hz, 1H), 3.04 (s, 6H), 3.58-3.63 (m, 1H), 3.97 (dd, J=11.0, 1.8 Hz, 1H), 4.60 (bs, 2H), 5.45 (dd, J=11.0, 2.1 Hz, 1H), 7.18 (t, J=7.3 Hz, 1H), 7.27 (t, J=7.5 Hz, 1H), 7.35 (d, J=7.3 Hz, 2H), 7.89 (s, 1H), 7.96 (bs, 1H). $^{13}$C NMR (126 MHz, DMSO-d$_6$) δ (ppm): 22.6, 24.6, 30.1, 2×36.9, 43.0, 67.5, 80.2, 112.4, 126.4, 2×127.4, 2×128.0, 135.3, 140.8, 150.6, 153.9, 159.2.

Example 36 2-(Dimethylamino)-6-[(4-methylbenzyl)amino]-9-(tetrahydro-2H-pyran-2-yl)-9H-purine Prepared from 2-chloro-6-[(4-methylbenzyl)amino]-9-(tetrahydro-2H-pyran-2-yl)-9H-purine and 5.6M solution of dimethylamine in absolute ethanol. White solid, chemical formula: $C_{20}H_{26}N_6O$, yield (%): 82. HPLC-UV/VIS retention time, purity (min., %): 30.32, 99.9. ESI$^+$-MS m/z (rel. int. %, ion): 367.8 (100, [M+H]$^+$), 283.8 (29, [M-THP+H]$^+$). $^1$H NMR (500 MHz, DMSO-d$_6$) δ (ppm): 1.51-1.59 (m, 2H), 1.63-1.72 (m, 1H), 1.83-1.86 (m, 1H), 1.91-1.94 (m, 1H), 2.14-2.19 (m, 1H), 2.23 (s, 3H), 3.04 (s, 6H), 3.58-3.63 (m, 1H), 3.97 (dd, J=11.0, 1.8 Hz, 1H), 4.55 (bs, 2H), 5.44 (dd, J=11.0, 2.1 Hz, 1H), 7.07 (d, J=7.9 Hz, 2H), 7.23 (d, J=7.6 Hz, 2H), 7.89 (s, 2H). $^{13}$C NMR (126 MHz, DMSO-d$_6$) δ (ppm): 20.6, 22.6, 24.6, 30.1, 2×36.9, 42.7, 67.5, 80.2, 112.4, 2×127.4, 2×128.6, 135.3, 135.4, 137.7, 150.6, 153.8, 159.2.

Example 37 2-(Dimethylamino)-6-{[4-(trifluoromethyl)benzyl]amino}-9-(tetrahydro-2H-pyran-2-yl)-9H-purine Prepared from 2-chloro-6-{[4-(trifluoromethyl)benzyl]amino}-9-(tetrahydro-2H-pyran-2-yl)-9H-purine and 5.6M solution of dimethylamine in absolute ethanol. White solid, chemical formula: $C_{20}H_{23}F_3N_6O$, yield (%): 96. HPLC-UV/VIS retention time, purity (min., %): 30.43, 99.9. ESI$^+$-MS m/z (rel. int. %, ion): 421.7 (100, [M+H]$^+$), 337.8 (81, [M-THP+H]$^+$). $^1$H NMR (500 MHz, DMSO-d$_6$) δ (ppm): 1.52-1.58 (m, 2H), 1.64-1.70 (m, 1H), 1.85 (dd, J=12.8, 1.8 Hz, 1H), 1.93 (bd, J=13.4 Hz, 1H), 2.15-2.23 (m, 1H), 3.00 (s, 6H), 3.58-3.63 (m, 1H), 3.97 (d, J=11.0 Hz, 1H), 4.66 (bs, 2H), 5.45 (dd, J=10.9, 1.7 Hz, 1H), 7.54 (d, J=8.3 Hz, 2H), 7.64 (d, J=7.9 Hz, 2H), 7.91 (s, 1H), 8.10 (bs, 1H). $^{13}$C NMR (126 MHz, DMSO-d$_6$) δ (ppm): 22.6, 24.6, 30.1, 2×36.8, 42.8, 67.5, 80.3, 112.4, 124.4 (q, $^1J_{CF}$=272.1 Hz), 2×125.0 (q, $^3J_{CF}$=3.6 Hz), 127.1 (q, $^2J_{CF}$=32.2 Hz), 2×127.9, 135.5, 145.7, 150.7, 153.8, 159.1.

Example 38 2-(Dimethylamino)-6-[(3-hydroxybenzyl)amino]-9-(tetrahydro-2H-pyran-2-yl)-9H-purine Prepared from 2-chloro-6-[(3-hydroxybenzyl)amino]-9-(tetrahydro-2H-pyran-2-yl)-9H-purine and 5.6M solution of dimethylamine in absolute ethanol. White solid, chemical formula: $C_{19}H_{24}N_6O_2$, yield (%): 94. HPLC-UV/VIS retention time, purity (min., %): 26.50, 99.5. ESI$^+$-MS m/z (rel. int. %, ion): 368.8 (100, [M+H]$^+$), 284.8 (53, [M-THP+H]$^+$). $^1$H NMR (500 MHz, DMSO-d$_6$) δ (ppm): 1.52-1.58 (m, 2H), 1.63-1.73 (m, 1H), 1.83-1.86 (m, 1H), 1.90-1.95 (m, 1H), 2.15-2.23 (m, 1H), 3.04 (s, 6H), 3.58-3.63 (m, 1H), 3.96-3.98 (m, 1H), 4.53 (bs, 2H), 5.45 (dd, J=11.0, 1.8 Hz, 1H), 6.55-6.57 (m, 1H), 6.75 (s, 1H), 6.76 (bs, 1H), 7.05 (t, J=7.9 Hz, 1H), 7.89 (s, 2H), 9.24 (bs, 1H). $^{13}$C NMR (126 MHz, DMSO-d$_6$) δ (ppm): 22.6, 24.6, 30.2, 36.9, 38.9, 39.1, 39.3, 39.5, 39.6, 39.8, 40.0, 42.9, 67.5, 80.3, 112.4, 113.4, 114.1, 118.0, 129.0, 135.3, 142.2, 150.7, 153.9, 157.2, 159.2.

Example 39 2-(Dimethylamino)-6-[(4-hydroxybenzyl)amino]-9-(tetrahydro-2H-pyran-2-yl)-9H-purine Prepared from 2-chloro-6-[(4-hydroxybenzyl)amino]-9-(tetrahydro-2H-pyran-2-yl)-9H-purine and 5.6M solution of dimethylamine in absolute ethanol. Pale yellow solid, chemical formula: $C_{19}H_{24}N_6O_2$, yield (%): 76. HPLC-UV/VIS retention time, purity (min., %): 26.12, 99.9. ESI$^+$-MS m/z (rel. int. %, ion): 369.8 (100, [M+H]$^+$), 285.7 (83, [M-THP+H]$^+$). $^1$H NMR (500 MHz, DMSO-d$_6$) δ (ppm): 1.51-1.56 (m, 2H), 1.66-1.70 (m, 1H), 1.83-1.86 (m, 1H), 1.91-1.94 (m, 1H), 2.18 (ddd, J=24.0, 12.5, 3.7 Hz, 1H), 3.06 (s, 6H), 3.58-3.63 (m, 1H), 3.95-3.98 (m, 1H), 4.48 (bs, 2H), 5.44 (dd, J=11.0, 1.5 Hz, 1H), 6.65 (d, J=8.6 Hz, 2H), 7.16 (d, J=8.3 Hz, 2H), 7.80 (bs, 1H), 7.88 (s, 1H), 9.19 (s, 1H). $^{13}$C NMR (126 MHz, DMSO-d$_6$) δ (ppm): 22.6, 24.6, 30.1, 2×36.9, 42.4, 67.5, 80.2, 112.4, 2×114.8, 2×128.7, 130.9, 135.2, 150.6, 153.8, 156.0, 159.2.

Example 40 2-(Methylamino)-6-[(4-methoxybenzyl)amino]-9-(tetrahydro-2H-pyran-2-yl)-9H-purine Prepared from 2-chloro-6-[(4-methoxybenzyl)amino]-9-(tetrahydro-2H-pyran-2-yl)-9H-purine and 8M solution of methylamine in absolute ethanol. White solid, chemical formula: C$_{19}$H$_{24}$N$_6$O$_2$, yield (%): 70. HPLC-UV/VIS retention time, purity (min., %): 24.92, 98.0. ESI$^+$-MS m/z (rel. int. %, ion): 369.8 (100, [M+H]$^+$), 285.8 (29, [M-THP+H]$^+$). $^1$H NMR (500 MHz, DMSO-d$_6$) δ (ppm): 1.51-1.57 (m, 2H), 1.62-1.72 (m, 1H), 1.83-1.86 (m, 1H), 1.91-1.94 (m, 1H), 2.16 (ddd, J=24.1, 12.4, 3.5 Hz, 1H), 2.76 (d, J=4.9 Hz, 3H), 3.56-3.62 (m, 1H), 3.69 (s, 3H), 3.97 (dd, J=11.0, 1.8 Hz, 1H), 4.53 (bs, 2H), 5.41 (d, J=10.4 Hz, 1H), 6.33 (bs, 1H), 6.83 (d, J=8.6 Hz, 2H), 7.27 (d, J=8.3 Hz, 2H), 7.76 (bs, 1H), 7.86 (s, 1H). $^{13}$C NMR (126 MHz, DMSO-d$_6$) δ (ppm): 22.6, 24.6, 28.3, 30.2, 42.1, 54.9, 67.6, 80.1, 112.9, 2×113.4, 2×128.7, 132.6, 134.8, 150.6, 154.3, 157.9, 159.9.

Example 41 2-(Dimethylamino)-6-[(4-methoxybenzyl)amino]-9-(tetrahydro-2H-pyran-2-yl)-9H-purine Prepared from 2-chloro-6-[(4-methoxybenzyl)amino]-9-(tetrahydro-2H-pyran-2-yl)-9H-purine and 5.6M solution of dimethylamine in absolute ethanol. White solid, chemical formula: C$_{20}$H$_{26}$N$_6$O$_2$, yield (%): 93. HPLC-UV/VIS retention time, purity (min., %): 28.85, 99.9. ESI$^+$-MS m/z (rel. int. %, ion): 383.8 (100, [M+H]$^+$), 299.8 (82, [M-THP+H]$^+$). $^1$H NMR (500 MHz, DMSO-d$_6$) δ (ppm): 1.51-1.59 (m, 2H), 1.63-1.72 (m, 1H), 1.83-1.86 (m, 1H), 1.91-1.94 (m, 1H), 2.18 (ddd, J=24.0, 12.5, 4.0 Hz, 1H), 3.06 (s, 6H), 3.58-3.63 (m, 1H), 3.68 (s, 3H), 3.97 (dd, J=11.0, 1.8 Hz, 1H), 4.52 (bs, 2H), 5.44 (dd, J=11.0, 2.1 Hz, 1H), 6.83 (d, J=8.9 Hz, 2H), 7.28 (d, J=8.6 Hz, 2H), 7.88 (s, 2H). $^{13}$C NMR (126 MHz, DMSO-d$_6$) δ (ppm): 22.6, 24.6, 30.1, 2×36.9, 42.4, 54.9, 67.5, 80.2, 112.4, 2×113.4, 2×128.7, 132.7, 135.2, 150.6, 153.8, 157.9, 159.2.

B) Substitution with 2-(dimethylamino)ethylamine or 3-(dimethylamino)propylamine—Typical Procedure A mixture of 2-chloro-6-substituted-9-(2-oxacycloalkyl)-9H-purine (150 mg, 1 eq.) and 2-(dimethylamino)ethylamine or 3-(dimethylamino)propylamine (10 eq.) in n-butanol (2.2 ml) was heated under Ar atmosphere in ACE pressure tube at 120° C. for 18 hours. The reaction mixture was evaporated under reduced pressure and the crude material was purified by silica column chromatography using chloroform/methanol as a mobile phase starting from pure chloroform with methanol gradient.

Example 42 2-{[2-(Dimethylamino)ethyl]amino}-6-furfurylamino-9-(tetrahydro-2H-pyran-2-yl)-9H-purine Prepared from compound 2-chloro-6-furfurylamino-9-(tetrahydro-2H-pyran-2-yl)-9H-purine and 2-(dimethylamino)ethylamine. White solid, chemical formula: C$_{19}$H$_{27}$N$_7$O$_2$, yield (%): 78. HPLC-UV/VIS retention time, purity (min., %): 16.27, 99.9. ESI$^+$-MS m/z (rel. int. %, ion): 385.8 (100, [M+H]$^+$). $^1$H NMR (500 MHz, DMSO-d$_6$) δ (ppm): 1.52-1.57 (m, 2H), 1.62-1.68 (m, 1H), 1.84-1.87 (m, 1H), 1.92-1.94 (m, 1H), 2.15-2.23 (m, 7H), 2.37 (t, J=6.9 Hz, 2H), 3.30-3.35 (m, 2H), 3.56-3.61 (m, 1H), 3.96-3.99 (m, 1H), 4.62 (bs, 2H), 5.41 (dd, J=11.0, 1.8 Hz, 1H), 6.17 (bs, 1H), 6.20 (dd, J=3.1, 0.6 Hz, 1H), 6.34 (dd, J=3.4, 1.8 Hz, 1H), 7.51 (dd, J=1.7, 0.8 Hz, 1H), 7.65 (bs, 1H), 7.87 (s, 1H). $^{13}$C NMR (126 MHz, DMSO-d$_6$) δ (ppm): 22.6, 24.5, 30.0, 36.3, 3×45.1, 58.3, 67.5, 80.3, 106.3, 110.31, 113.0, 135.0, 141.5, 150.9, 153.4, 154.2, 159.1.

TABLE 1

Examples of 9-(oxetan-2-yl) purine derivatives

| | PURINE SUBSTITUENT | | CHN ANALYSES | MS ANALYSIS |
|---|---|---|---|---|
| Comp. | C2 | C6 | [% C, % H, % N] | [M + H]$^+$ |
| 1 | MeNH— | furfurylamino | 60.0, 5.4, 28.0 | 301 |
| 2 | EtNH— | furfurylamino | 57.3, 5.8, 26.7 | 315 |
| 3 | Me$_2$N— | furfurylamino | 57.3, 5.8 26.7 | 315 |
| 4 | Et$_2$N— | furfurylamino | 59.6, 6.5, 24.5 | 343 |
| 5 | Me$_2$N-ethyl-NH— | furfurylamino | 57.1, 6.5, 27.4 | 358 |
| 6 | MeNH— | benzylamino | 61.9, 5.9, 27.1 | 311 |
| 7 | EtNH— | benzylamino | 63.0, 6.2, 25.9 | 325 |
| 8 | Me$_2$N— | benzylamino | 63.0, 6.2, 25.9 | 325 |
| 9 | Et$_2$N— | benzylamino | 64.8, 6.9, 23.9 | 353 |
| 10 | Me$_2$N-ethyl-NH— | benzylamino | 62.1, 6.9, 26.7 | 368 |
| 11 | MeNH— | (3-methylbut-2-en-1-yl)amino | 58.3, 7.0, 29.2 | 289 |
| 12 | EtNH— | (3-methylbut-2-en-1-yl)amino | 59.6, 7.3, 27.8 | 303 |
| 13 | Me$_2$N— | (3-methylbut-2-en-1-yl)amino | 59.6, 7.3, 27.8 | 303 |
| 14 | Et$_2$N— | (3-methylbut-2-en-1-yl)amino | 61.8, 7.9, 25.4 | 331 |
| 15 | Me$_2$N-ethyl-NH— | (3-methylbut-2-en-1-yl)amino | 59.1, 7.9, 28.4 | 346 |
| 16 | MeNH— | (E)-(4-hydroxy-3-methylbut-2-en-1-yl)amino | 55.3, 6.6, 27.6 | 305 |
| 17 | EtNH— | (E)-(4-hydroxy-3-methylbut-2-en-1-yl)amino | 56.6, 7.0, 26.4 | 319 |
| 18 | Me$_2$N— | (E)-(4-hydroxy-3-methylbut-2-en-1-yl)amino | 56.6, 7.0, 26.4 | 319 |
| 19 | Et$_2$N— | (E)-(4-hydroxy-3-methylbut-2-en-1-yl)amino | 58.9, 7.6, 24.3 | 347 |

TABLE 1-continued

Examples of 9-(oxetan-2-yl) purine derivatives

| | PURINE SUBSTITUENT | | CHN ANALYSES | MS ANALYSIS |
|---|---|---|---|---|
| Comp. | C2 | C6 | [% C, % H, % N] | [M + H]$^+$ |
| 20 | Me$_2$N-ethyl-NH— | (E)-(4-hydroxy-3-methylbut-2-en-1-yl)amino | 56.5, 7.5, 27.1 | 362 |
| 21 | MeNH— | (Z)-(4-hydroxy-3-methylbut-2-en-1-yl)amino | 55.3, 6.6, 27.6 | 305 |
| 22 | EtNH— | (Z)-(4-hydroxy-3-methylbut-2-en-1-yl)amino | 56.6, 7.0, 26.4 | 319 |
| 23 | Me$_2$N— | (Z)-(4-hydroxy-3-methylbut-2-en-1-yl)amino | 56.6, 7.0, 26.4 | 319 |
| 24 | Et$_2$N— | (Z)-(4-hydroxy-3-methylbut-2-en-1-yl)amino | 58.9, 7.6, 24.3 | 347 |
| 25 | Me$_2$N-ethyl-NH— | (Z)-(4-hydroxy-3-methylbut-2-en-1-yl)amino | 56.5, 7.5, 27.1 | 362 |

TABLE 2

Examples of 9-(tetrahydrofuran-2-yl) purine derivatives

| | PURINE SUBSTITUENT | | CHN ANALYSES | MS ANALYSIS |
|---|---|---|---|---|
| Comp. | C2 | C6 | [% C, % H, % N] | [M + H]$^+$ |
| 26 | MeNH— | furfurylamino | 57.3, 5.8, 26.7 | 315 |
| 27 | EtNH— | furfurylamino | 58.2, 6.1, 25.6 | 329 |
| 28 | propylNH— | furfurylamino | 59.6, 6.5, 24.5 | 343 |
| 29 | 2-propylNH— | furfurylamino | 59.6, 6.5, 24.5 | 343 |
| 30 | Me$_2$N— | furfurylamino | 58.2, 6.1, 25.6 | 329 |
| 31 | Et$_2$N— | furfurylamino | 60.7, 6.8, 23.6 | 357 |
| 32 | Me$_2$N-ethyl-NH— | furfurylamino | 58.2, 6.8, 26.4 | 372 |
| 33 | Me$_2$N-propyl-NH— | furfurylamino | 59.2, 7.1, 25.4 | 386 |
| 34 | MeNH— | (3-methylfurfuryl)amino | 58.5, 6.1, 25.6 | 329 |
| 35 | EtNH— | (3-methylfurfuryl)amino | 59.6, 6.5, 24.5 | 343 |
| 36 | Me$_2$N— | (3-methylfurfuryl)amino | 59.6, 6.5, 24.5 | 343 |
| 37 | Et$_2$N— | (3-methylfurfuryl)amino | 61.6, 7.1, 22.7 | 371 |
| 38 | Me$_2$N-ethyl-NH— | (3-methylfurfuryl)amino | 59.2, 7.1, 25.4 | 386 |
| 39 | MeNH— | (4-methylfurfuryl)amino | 58.5, 6.1, 25.6 | 329 |
| 40 | EtNH— | (4-methylfurfuryl)amino | 59.6, 6.5, 24.5 | 343 |
| 41 | Me$_2$N— | (4-methylfurfuryl)amino | 59.6, 6.5, 24.5 | 343 |
| 42 | Et$_2$N— | (4-methylfurfuryl)amino | 61.6, 7.1, 22.7 | 371 |
| 43 | Me$_2$N-ethyl-NH— | (4-methylfurfuryl)amino | 59.2, 7.1, 25.4 | 386 |
| 44 | MeNH— | (5-methylfurfuryl)amino | 58.5, 6.1, 25.6 | 329 |
| 45 | EtNH— | (5-methylfurfuryl)amino | 59.6, 6.5, 24.5 | 343 |
| 46 | Me$_2$N— | (5-methylfurfuryl)amino | 59.6, 6.5, 24.5 | 343 |
| 47 | Et$_2$N— | (5-methylfurfuryl)amino | 61.6, 7.1, 22.7 | 371 |
| 48 | Me$_2$N-ethyl-NH— | (5-methylfurfuryl)amino | 59.2, 7.1, 25.4 | 386 |
| 49 | MeNH— | (3-methoxyfurfuryl)amino | 55.8, 5.9, 24.4 | 345 |
| 50 | EtNH— | (3-methoxyfurfuryl)amino | 57.0, 6.2, 23.5 | 359 |
| 51 | Me$_2$N— | (3-methoxyfurfuryl)amino | 57.0, 6.2, 23.5 | 359 |
| 52 | Et$_2$N— | (3-methoxyfurfuryl)amino | 59.1, 6.8, 21.8 | 387 |
| 53 | Me$_2$N-ethyl-NH— | (3-methoxyfurfuryl)amino | 56.8, 6.8, 24.4 | 402 |
| 54 | MeNH— | (4-methoxylfurfuryl)amino | 55.8, 5.9, 24.4 | 345 |
| 55 | EtNH— | (4-methoxylfurfuryl)amino | 57.0, 6.2, 23.5 | 359 |
| 56 | Me$_2$N— | (4-methoxylfurfuryl)amino | 57.0, 6.2, 23.5 | 359 |
| 57 | Et$_2$N— | (4-methoxylfurfuryl)amino | 59.1, 6.8, 21.8 | 387 |
| 58 | Me$_2$N-ethyl-NH— | (4-methoxylfurfuryl)amino | 56.8, 6.8, 24.4 | 402 |
| 59 | MeNH— | (5-methoxyfurfuryl)amino | 55.8, 5.9, 24.4 | 345 |
| 60 | EtNH— | (5-methoxyfurfuryl)amino | 57.0, 6.2, 23.5 | 359 |
| 61 | Me$_2$N— | (5-methoxyfurfuryl)amino | 57.0, 6.2, 23.5 | 359 |
| 62 | Et$_2$N— | (5-methoxyfurfuryl)amino | 59.1, 6.8, 21.8 | 387 |
| 63 | Me$_2$N-ethyl-NH— | (5-methoxyfurfuryl)amino | 56.8, 6.8, 24.4 | 402 |
| 64 | MeNH— | benzylamino | 63.0, 6.2, 25.9 | 325 |
| 65 | EtNH— | benzylamino | 63.9, 6.6, 24.8 | 339 |
| 66 | Me$_2$N— | benzylamino | 63.9, 6.6, 24.8 | 339 |
| 67 | Et$_2$N— | benzylamino | 65.6, 7.2, 22.9 | 367 |
| 68 | Me$_2$N-ethyl-NH— | benzylamino | 63.0, 7.1, 25.7 | 382 |
| 69 | MeNH— | (3-hydroxybenzyl)amino | 60.0, 5.9, 24.7 | 341 |
| 70 | EtNH— | (3-hydroxybenzyl)amino | 61.0, 6.3, 23.7 | 355 |
| 71 | Me$_2$N— | (3-hydroxybenzyl)amino | 61.0, 6.3, 23.7 | 355 |
| 72 | Et$_2$N— | (3-hydroxybenzyl)amino | 62.8, 6.9, 22.0 | 383 |
| 73 | Me$_2$N-ethyl-NH— | (3-hydroxybenzyl)amino | 60.4, 6.9, 24.7 | 398 |
| 74 | MeNH— | (4-hydroxybenzyl)amino | 60.0, 5.9, 24.7 | 341 |
| 75 | EtNH— | (4-hydroxybenzyl)amino | 61.0, 6.3, 23.7 | 355 |

TABLE 2-continued

Examples of 9-(tetrahydrofuran-2-yl) purine derivatives

| | PURINE SUBSTITUENT | | CHN ANALYSES | MS ANALYSIS |
|---|---|---|---|---|
| Comp. | C2 | C6 | [% C, % H, % N] | [M + H]+ |
| 76 | Me₂N— | (4-hydroxybenzyl)amino | 61.0, 6.3, 23.7 | 355 |
| 77 | Et₂N— | (4-hydroxybenzyl)amino | 62.8, 6.9, 22.0 | 383 |
| 78 | Me₂N-ethyl-NH— | (4-hydroxybenzyl)amino | 60.4, 6.9, 24.7 | 398 |
| 79 | MeNH— | (3-methoxybenzyl)amino | 61.0, 6.3, 23.7 | 355 |
| 80 | EtNH— | (3-methoxybenzyl)amino | 61.9, 6.6, 22.8 | 369 |
| 81 | Me₂N— | (3-methoxybenzyl)amino | 61.9, 6.6, 22.8 | 369 |
| 82 | Et₂N— | (3-methoxybenzyl)amino | 63.6, 7.1, 21.2 | 397 |
| 83 | Me₂N-ethyl-NH— | (3-methoxybenzyl)amino | 61.3, 7.1, 23.8 | 412 |
| 84 | MeNH— | (4-methoxybenzyl)amino | 61.0, 6.3, 23.7 | 355 |
| 85 | EtNH— | (4-methoxybenzyl)amino | 61.9, 6.6, 22.8 | 369 |
| 86 | Me₂N— | (4-methoxybenzyl)amino | 61.9, 6.6, 22.8 | 369 |
| 87 | Et₂N— | (4-methoxybenzyl)amino | 63.6, 7.1, 21.2 | 397 |
| 88 | Me₂N-ethyl-NH— | (4-methoxybenzyl)amino | 61.3, 7.1, 23.8 | 412 |
| 89 | Me₂N— | (4-hydroxy-3-methoxybenzyl)amino | 59.3, 6.2, 21.8 | 385 |
| 90 | MeNH— | (3-methylbut-2-en-1-yl)amino | 59.6, 7.3, 27.8 | 303 |
| 91 | EtNH— | (3-methylbut-2-en-1-yl)amino | 60.7, 7.7, 26.6 | 317 |
| 92 | Me₂N— | (3-methylbut-2-en-1-yl)amino | 60.7, 7.7, 26.6, | 317 |
| 93 | Et₂N— | (3-methylbut-2-en-1-yl)amino | 62.8, 8.2, 24.4 | 345 |
| 94 | Me₂N-ethyl-NH— | (3-methylbut-2-en-1-yl)amino | 60.1, 8.1, 27.3 | 360 |
| 95 | MeNH— | (E)-(4-hydroxy-3-methylbut-2-en-1-yl)amino | 56.6, 7.0, 26.4 | 319 |
| 96 | EtNH— | (E)-(4-hydroxy-3-methylbut-2-en-1-yl)amino | 57.8, 7.3, 25.3 | 333 |
| 97 | Me₂N— | (E)-(4-hydroxy-3-methylbut-2-en-1-yl)amino | 57.8, 7.3, 25.3 | 333 |
| 98 | Et₂N— | (E)-(4-hydroxy-3-methylbut-2-en-1-yl)amino | 60.0, 7.8, 23.3 | 361 |
| 99 | Me₂N-ethyl-NH— | (E)-(4-hydroxy-3-methylbut-2-en-1-yl)amino | 57.6, 7.8, 26.1 | 376 |
| 100 | MeNH— | (Z)-(4-hydroxy-3-methylbut-2-en-1-yl)amino | 56.6, 7.0, 26.4 | 319 |
| 101 | EtNH— | (Z)-(4-hydroxy-3-methylbut-2-en-1-yl)amino | 57.8, 7.3, 25.3 | 333 |
| 102 | Me₂N— | (Z)-(4-hydroxy-3-methylbut-2-en-1-yl)amino | 57.8, 7.3, 25.3 | 333 |
| 103 | Et₂N— | (Z)-(4-hydroxy-3-methylbut-2-en-1-yl)amino | 60.0, 7.8, 23.3 | 361 |
| 104 | Me₂N-ethyl-NH— | (Z)-(4-hydroxy-3-methylbut-2-en-1-yl)amino | 57.6, 7.8, 26.1 | 376 |
| 105 | MeNH— | (4-hydroxy-3-methylbutyl)amino | 56.2, 7.6, 26.2 | 321 |
| 106 | EtNH— | (4-hydroxy-3-methylbutyl)amino | 57.5, 7.8, 25.1 | 335 |
| 107 | Me₂N— | (4-hydroxy-3-methylbutyl)amino | 57.5, 7.8, 25.1 | 335 |
| 108 | Et₂N— | (4-hydroxy-3-methylbutyl)amino | 59.6, 8.3, 23.2 | 363 |
| 109 | Me₂N-ethyl-NH— | (4-hydroxy-3-methylbutyl)amino | 57.3, 8.3, 26.0 | 378 |

TABLE 3

Examples of prepared 9-(tetrahydro-2H-pyran-2-yl) purine derivatives

| | PURINE SUBSTITUENT | | CHN ANALYSES | MS ANALYSIS |
|---|---|---|---|---|
| Comp. | C2 | C6 | [% C, % H, % N] | [M + H]+ |
| 110 | MeNH— | furfurylamino | 58.5, 6.1, 25.6 | 329 |
| 111 | EtNH— | furfurylamino | 59.6, 6.5, 24.5 | 343 |
| 112 | propylNH— | furfurylamino | 60.7, 6.8, 23.6 | 357 |
| 113 | 2-propylNH— | furfurylamino | 60.7, 6.8, 23.6 | 357 |
| 114 | Me₂N— | furfurylamino | 59.6, 6.5, 24.5 | 343 |
| 115 | Et₂N— | furfurylamino | 61.6, 7.1, 22.7 | 371 |
| 116 | Me₂N-ethyl-NH— | furfurylamino | 59.2, 7.1, 25.4 | 386 |
| 117 | Me₂N-propyl-NH— | furfurylamino | 60.1, 7.3, 24.5 | 400 |
| 118 | MeNH— | (3-methylfurfuryl)amino | 59.6, 6.5, 24.5 | 343 |
| 119 | EtNH— | (3-methylfurfuryl)amino | 60.7, 6.8, 23.6 | 357 |
| 120 | Me₂N— | (3-methylfurfuryl)amino | 60.7, 6.8, 23.6 | 357 |
| 121 | Et₂N— | (3-methylfurfuryl)amino | 62.5, 7.3, 21.9 | 385 |
| 122 | Me₂N-ethyl-NH— | (3-methylfurfuryl)amino | 60.1, 7.3, 24.5 | 400 |
| 123 | MeNH— | (4-methylfurfuryl)amino | 59.6, 6.5, 24.5 | 343 |
| 124 | EtNH— | (4-methylfurfuryl)amino | 60.7, 6.8, 23.6 | 357 |
| 125 | Me₂N— | (4-methylfurfuryl)amino | 60.7, 6.8, 23.6 | 357 |
| 126 | Et₂N— | (4-methylfurfuryl)amino | 62.5, 7.3, 21.9 | 385 |

TABLE 3-continued

Examples of prepared 9-(tetrahydro-2H-pyran-2-yl) purine derivatives

| | PURINE SUBSTITUENT | | CHN ANALYSES | MS ANALYSIS |
|---|---|---|---|---|
| Comp. | C2 | C6 | [% C, % H, % N] | [M + H]$^+$ |
| 127 | Me$_2$N-ethyl-NH— | (4-methylfurfuryl)amino | 60.1, 7.3, 24.5 | 400 |
| 128 | MeNH— | (5-methylfurfuryl)amino | 59.6, 6.5, 24.5 | 343 |
| 129 | EtNH— | (5-methylfurfuryl)amino | 60.7, 6.8, 23.6 | 357 |
| 130 | Me$_2$N— | (5-methylfurfuryl)amino | 60.7, 6.8, 23.6 | 357 |
| 131 | Et$_2$N— | (5-methylfurfuryl)amino | 62.5, 7.3, 21.9 | 385 |
| 132 | Me$_2$N-ethyl-NH— | (5-methylfurfuryl)amino | 60.1, 7.3, 24.5 | 400 |
| 133 | MeNH— | (3-methoxyfurfuryl)amino | 57.0, 6.2, 23.5 | 359 |
| 134 | EtNH— | (3-methoxyfurfuryl)amino | 58.1, 6.5, 22.6 | 373 |
| 135 | Me$_2$N— | (3-methoxyfurfuryl)amino | 58.1, 6.5, 22.6 | 373 |
| 136 | Et$_2$N— | (3-methoxyfurfuryl)amino | 60.0, 7.1, 21.0 | 401 |
| 137 | Me$_2$N-ethyl-NH— | (3-methoxyfurfuryl)amino | 57.8, 7.0, 23.6 | 416 |
| 138 | MeNH— | (4-methoxylfurfuryl)amino | 57.0, 6.2, 23.5 | 359 |
| 139 | EtNH— | (4-methoxylfurfuryl)amino | 58.1, 6.5, 22.6 | 373 |
| 140 | Me$_2$N— | (4-methoxylfurfuryl)amino | 58.1, 6.5, 22.6 | 373 |
| 141 | Et$_2$N— | (4-methoxylfurfuryl)amino | 60.0, 7.1, 21.0 | 401 |
| 142 | Me$_2$N-ethyl-NH— | (4-methoxylfurfuryl)amino | 57.8, 7.0, 23.6 | 416 |
| 143 | MeNH— | (5-methoxyfurfuryl)amino | 57.0, 6.2, 23.5 | 359 |
| 144 | EtNH— | (5-methoxyfurfuryl)amino | 58.1, 6.5, 22.6 | 373 |
| 145 | Me$_2$N— | (5-methoxyfurfuryl)amino | 58.1, 6.5, 22.6 | 373 |
| 146 | Et$_2$N— | (5-methoxyfurfuryl)amino | 60.0, 7.1, 21.0 | 401 |
| 147 | Me$_2$N-ethyl-NH— | (5-methoxyfurfuryl)amino | 57.8, 7.0, 23.6 | 416 |
| 148 | MeNH— | benzylamino | 63.9, 6.6, 24.8 | 339 |
| 149 | EtNH— | benzylamino | 64.8, 6.9, 23.9 | 353 |
| 150 | Me$_2$N— | benzylamino | 64.8, 6.9, 23.9 | 353 |
| 151 | Et$_2$N— | benzylamino | 66.3, 7.4, 22.1 | 381 |
| 152 | Me$_2$N-ethyl-NH— | benzylamino | 63.8, 7.4, 24.8 | 396 |
| 153 | MeNH— | (3-hydroxybenzyl)amino | 61.0, 6.3, 23.7 | 355 |
| 154 | EtNH— | (3-hydroxybenzyl)amino | 61.9, 6.6, 22.8 | 369 |
| 155 | Me$_2$N— | (3-hydroxybenzyl)amino | 61.9, 6.6, 22.8 | 369 |
| 156 | Et$_2$N— | (3-hydroxybenzyl)amino | 63.6, 7.2, 21.2 | 397 |
| 157 | Me$_2$N-ethyl-NH— | (3-hydroxybenzyl)amino | 61.3, 7.1, 23.8 | 412 |
| 158 | MeNH— | (4-hydroxybenzyl)amino | 61.0, 6.3, 23.7 | 355 |
| 159 | EtNH— | (4-hydroxybenzyl)amino | 61.9, 6.6, 22.8 | 369 |
| 160 | Me$_2$N— | (4-hydroxybenzyl)amino | 61.9, 6.6, 22.8 | 369 |
| 161 | Et$_2$N— | (4-hydroxybenzyl)amino | 63.6, 7.2, 21.2 | 397 |
| 162 | Me$_2$N-ethyl-NH— | (4-hydroxybenzyl)amino | 61.3, 7.1, 23.8 | 412 |
| 163 | MeNH— | (3-methoxybenzyl)amino | 61.9, 6.6, 22.8 | 369 |
| 164 | EtNH— | (3-methoxybenzyl)amino | 62.8, 6.9, 22.0 | 383 |
| 165 | Me$_2$N— | (3-methoxybenzyl)amino | 62.8, 6.9, 22.0 | 383 |
| 166 | Et$_2$N— | (3-methoxybenzyl)amino | 64.4, 7.4, 20.5 | 411 |
| 167 | Me$_2$N-ethyl-NH— | (3-methoxybenzyl)amino | 62.1, 7.3, 23.0 | 425 |
| 168 | MeNH— | (4-methoxybenzyl)amino | 61.9, 6.6, 22.8 | 369 |
| 169 | EtNH— | (4-methoxybenzyl)amino | 62.8, 6.9, 22.0 | 383 |
| 170 | Me$_2$N— | (4-methoxybenzyl)amino | 62.8, 6.9, 22.0 | 383 |
| 171 | Et$_2$N— | (4-methoxybenzyl)amino | 64.4, 7.4, 20.5 | 411 |
| 172 | Me$_2$N-ethyl-NH— | (4-methoxybenzyl)amino | 62.1, 7.3, 23.0 | 425 |
| 173 | MeNH— | (3-methylbut-2-en-1-yl)amino | 60.7, 7.7, 26.6 | 317 |
| 174 | EtNH— | (3-methylbut-2-en-1-yl)amino | 61.8, 7.9, 25.4 | 331 |
| 175 | Me$_2$N— | (3-methylbut-2-en-1-yl)amino | 61.8, 7.9, 25.4 | 331 |
| 176 | Et$_2$N— | (3-methylbut-2-en-1-yl)amino | 63.7, 8.4, 23.4 | 359 |
| 177 | Me$_2$N-ethyl-NH— | (3-methylbut-2-en-1-yl)amino | 61.1, 8.4, 26.3 | 374 |
| 178 | MeNH— | (E)-(4-hydroxy-3-methylbut-2-en-1-yl)amino | 57.8, 7.3, 25.3 | 333 |
| 179 | EtNH— | (E)-(4-hydroxy-3-methylbut-2-en-1-yl)amino | 58.9, 7.6, 24.3 | 347 |
| 180 | Me$_2$N— | (E)-(4-hydroxy-3-methylbut-2-en-1-yl)amino | 58.9, 7.6, 24.3 | 347 |
| 181 | Et$_2$N— | (E)-(4-hydroxy-3-methylbut-2-en-1-yl)amino | 60.9, 8.1, 22.4 | 375 |
| 182 | Me$_2$N-ethyl-NH— | (E)-(4-hydroxy-3-methylbut-2-en-1-yl)amino | 58.6, 8.0, 25.2 | 390 |
| 183 | MeNH— | (Z)-(4-hydroxy-3-methylbut-2-en-1-yl)amino | 57.8, 7.3, 25.3 | 333 |
| 184 | EtNH— | (Z)-(4-hydroxy-3-methylbut-2-en-1-yl)amino | 58.9, 7.6, 24.3 | 347 |
| 185 | Me$_2$N— | (Z)-(4-hydroxy-3-methylbut-2-en-1-yl)amino | 58.9, 7.6, 24.3 | 347 |
| 186 | Et$_2$N— | (Z)-(4-hydroxy-3-methylbut-2-en-1-yl)amino | 60.9, 8.1, 22.4 | 375 |
| 187 | Me$_2$N-ethyl-NH— | (Z)-(4-hydroxy-3-methylbut-2-en-1-yl)amino | 58.6, 8.0, 25.2 | 390 |
| 188 | MeNH— | (4-hydroxy-3-methylbutyl)amino | 57.5, 7.8, 25.1 | 335 |
| 189 | EtNH— | (4-hydroxy-3-methylbutyl)amino | 58.6, 8.1, 24.1 | 349 |
| 190 | Me$_2$N— | (4-hydroxy-3-methylbutyl)amino | 58.6, 8.1, 24.1 | 349 |

TABLE 3-continued

Examples of prepared 9-(tetrahydro-2H-pyran-2-yl) purine derivatives

| | PURINE SUBSTITUENT | | CHN ANALYSES | MS ANALYSIS |
|---|---|---|---|---|
| Comp. | C2 | C6 | [% C, % H, % N] | [M + H]$^+$ |
| 191 | Et$_2$N— | (4-hydroxy-3-methylbutyl)amino | 60.6, 8.6, 22.3 | 377 |
| 192 | Me$_2$N-ethyl-NH— | (4-hydroxy-3-methylbutyl)amino | 58.3, 8.5, 25.0 | 392 |

TABLE 4

Examples of prepared 9-(oxepan-2-yl) purine derivatives

| | PURINE SUBSTITUENT | | CHN ANALYSES | |
|---|---|---|---|---|
| Comp. | C2 | C6 | [% C, % H, % N] | MS ANALYSIS |
| 193 | MeNH— | furfurylamino | 59.6, 6.5, 24.5 | 343 |
| 194 | EtNH— | furfurylamino | 60.7, 6.8, 23.6 | 357 |
| 195 | Me$_2$N— | furfurylamino | 60.7, 6.8, 23.6 | 357 |
| 196 | Et$_2$N— | furfurylamino | 62.5, 7.3, 21.9 | 385 |
| 197 | Me$_2$N-ethyl-NH— | furfurylamino | 60.1, 7.3, 24.5 | 400 |
| 198 | MeNH— | benzylamino | 64.8, 6.9, 23.9 | 353 |
| 199 | EtNH— | benzylamino | 65.6, 7.2, 22.9 | 367 |
| 200 | Me$_2$N— | benzylamino | 65.6, 7.2, 22.9 | 367 |
| 201 | Et$_2$N— | benzylamino | 67.0, 7.7, 21.3 | 395 |
| 202 | Me$_2$N-ethyl-NH— | benzylamino | 64.5, 7.6, 23.9 | 410 |

Example 43 In Vitro Cytotoxic Activity of Novel Compounds

Low cytotoxicity of the compounds is the major property determining the agricultural use. One of the parameters used, as the basis for cytotoxicity assays, is the metabolic activity of viable cells. For example, a microtiter assay, which uses the Calcein AM, is now widely used to quantitate cell proliferation and cytotoxicity. For instance, this assay is used in drug screening programs and in chemosensitivity testing. Because only metabolically active cells cleave Calcein AM, these assays detect viable cells exclusively. The quantity of reduced Calcein AM corresponds to the number of vital cells in the culture.

Mouse fibroblasts NIH3T3; mouse immortalized bone marrow macrophages B2.4 and B10A.4, and BJ (human foreskin fibroblasts) were used for routine screening of compounds. The cells were maintained in Nunc/Corning 80 cm$^2$ plastic tissue culture flasks and cultured in cell culture medium (DMEM with 5 g/l glucose, 2 mM glutamine, 100 U/ml penicillin, 100 µg/ml streptomycin, 10% fetal calf serum and sodium bicarbonate).

The cell suspensions that were prepared and diluted according to the particular cell type and the expected target cell density (2.500-30.000 cells per well based on cell growth characteristics) were added by pipette (80 µl) into 96/well microtiter plates. Inoculates were allowed a pre-incubation period of 24 hours at 37° C. and 5% CO$_2$ for stabilisation. Four-fold dilutions of the intended test concentration were added at time zero in 20 µl aliquots to the microtiter plate wells. Usually, the compound tested was evaluated at six 4-fold dilutions. In routine testing, the highest well concentration was 166.7 µM, but it can be the matter of change dependent on the agent. All compound concentrations were examined in duplicates. Incubations of cells with the tested compounds lasted for 72 hours at 37° C., in 5% CO$_2$ atmosphere and 100% humidity. At the end of the incubation period, the cells were assayed by using Calcein AM. Ten microliters of the stock solution were pipetted into each well and incubated for 1 hour. Fluorescence (FD) was measured with the Labsystem FIA Reader Fluoroscan Ascent (UK). The tumour cell survival (GI$_{50}$) was calculated using the following equitation: TCS=(FD$_{drug\ exposed\ well}$/mean FD$_{control\ wells}$)×100%. The IC$_{50}$ value, the compound concentration lethal to 50% of the cells, was calculated from the obtained dose response curves (Table 5).

Zero cytotoxicity is a basic prerequisite for the use of these substances in cosmetical applications. To assess the antitumor activity, the toxicity of new derivatives on panels containing cell lines of different histogenic and species origin was tested (Table 5). It has been shown that for all tested tumor lines the action of the new compounds was comparable, whereas non-malignant cell lines, NIH3T3 fibroblasts and normal human lymphocytes were resistant to this effect. The compounds listed in Table 5 can be divided into 2 groups. The first group contains "classical cytokinins" represented by 6-substituted purines (their effects are already known). The second group includes novel substituted purine derivatives. These results suggest that substitution at the 2-position of the purine skeleton generally results in a decrease in cytotoxic activity compared to "classical cytokinin" analogues. As shown in Table 5, GI50 for NIH3T3 fibroblasts and normal human lymphocytes was always greater than 166.7 µM. The new derivatives show zero toxicity for both normal and tumor cells at concentrations of about 166.7 µM and are therefore much more suitable for agricultural and cosmetic applications than "classical cytokinins" (6-substituted purine derivatives).

Low cytotoxicity (high IC$_{50}$ value) of the compounds is the basic prerequisite for cosmetic and medical applications. Zero cytotoxic activity was found for N$^2$,N$^6$-disubstituted-9-(2-oxacycloalkyl)-9H-purin-2,6-diamines in comparison to classical cytokinins known in prior art (kinetin, isopentenyladenine, . . . ).

TABLE 5

Cytotoxicity of novel compounds for different normal cell lines tested/$IC_{50}$ (μmol/L)

| Compound | B10A.4 | B10A.4 | BJ | NIH-3T3 |
|---|---|---|---|---|
| Kinetin | >166.7 | 164.1 | 147.5 | 132.8 |
| isopentenyladenine | >166.7 | 146.9 | 134.1 | 123.7 |
| 6-benzyladenine | >166.7 | 138.9 | 128.7 | 112.6 |
| trans-zeatin | >166.7 | >166.7 | >166.7 | 154.9 |
| meta-topolin | >166.7 | 178.4 | 165.7 | 167.2 |
| ortho-topolin | 87.5 | 94.3 | 107.8 | 94.1 |
| Adenine | >166.7 | >166.7 | >166.7 | >166.7 |
| 3 | >166.7 | | >166.7 | >166.7 |
| 9 | >166.7 | | >166.7 | >166.7 |
| 13 | >166.7 | >166.7 | >166.7 | >166.7 |
| 14 | >166.7 | >166.7 | >166.7 | >166.7 |
| 30 | >166.7 | | >166.7 | >166.7 |
| 39 | >166.7 | | >166.7 | >166.7 |
| 46 | >166.7 | | >166.7 | >166.7 |
| 47 | >166.7 | | >166.7 | >166.7 |
| 49 | >166.7 | >166.7 | >166.7 | >166.7 |
| 58 | >166.7 | | >166.7 | >166.7 |
| 59 | >166.7 | | >166.7 | >166.7 |
| 60 | >166.7 | | >166.7 | >166.7 |
| 75 | >166.7 | | >166.7 | >166.7 |
| 82 | >166.7 | | >166.7 | >166.7 |
| 84 | >166.7 | | >166.7 | >166.7 |
| 85 | >166.7 | | >166.7 | >166.7 |
| 87 | >166.7 | | >166.7 | >166.7 |
| 93 | >166.7 | | >166.7 | >166.7 |
| 99 | >166.7 | | >166.7 | >166.7 |
| 101 | >166.7 | | >166.7 | >166.7 |
| 103 | >166.7 | | >166.7 | >166.7 |
| 104 | >166.7 | | >166.7 | >166.7 |
| 105 | >166.7 | | >166.7 | >166.7 |
| 107 | >166.7 | | >166.7 | >166.7 |
| 108 | >166.7 | | >166.7 | >166.7 |
| 111 | >166.7 | | >166.7 | >166.7 |
| 114 | >166.7 | | >166.7 | >166.7 |
| 116 | >166.7 | | >166.7 | >166.7 |
| 119 | >166.7 | | >166.7 | >166.7 |
| 127 | >166.7 | | >166.7 | >166.7 |
| 132 | >166.7 | | >166.7 | >166.7 |

Example 44 Radical Scavenging Activity Determined by ORAC

The ability of compounds to scavenge free radicals in vitro was determined by Oxygen Radical Absorbance Capacity (ORAC) method. In brief, fluorescein (100 μl, 500 mM) and 25 μl of compound solution were added into each working well in a 96-well microplate preincubated at 37° C. Thereafter, 25 μL of 250 mM AAPH was quickly added, microplate was shaken for 5 s and the fluorescence (Ex. 485 nm, Em. 510 nm) was read every 3 min over 90 min by using microplate reader Infinite 200 (TECAN, Switzerland). The net area under the curve was used to express antioxidant activity relative to trolox which was used as a standard. Compounds with ORAC value higher than 1 are more effective than trolox, the hydrophilic equivalent of vitamin E. Kinetin, a naturally occurring cytokinin with antioxidant properties, was assigned for comparison as a control and as a substance known in the art.

TABLE 6

Radical scavenging activity on new derivatives

| Compound | ORAC (compound/trolox) |
|---|---|
| kinetin | 0.201 ± 0.5 |
| 155 | 2.422 ± 0.107* |
| 30 | 0.292 ± 0.006 |
| 89 | 4.359 ± 0.183 |
| 71 | 5.212 ± 0.238 |
| 116 | 2.475 ± 0.086 |
| 110 | 0.205 ± 0.032 |
| 114 | 0.211 ± 0.018 |
| 76 | 0.192 ± 0.005 |
| 160 | 0.728 ± 0.016 |
| 128 | 0.461 ± 0.003 |
| 46 | 0.14 ± 0.004 |
| 64 | 0.24 ± 0.001 |

*Mean ± SD (n = 3)

Example 45 Activation of Transcription Factor Nrf2

The ability of compounds to activate Nrf2-dependent expression was determined by EpRE-LUX reporter cell line. In brief, compounds at 100, 10, 1 and 0.1 μM concentrations were incubated for 24 h with cells. After cells lysis (10 mM Tris, 2 mM DTT), a buffer containing 0.2 mM luciferin was added to start luminescent reaction. The increase in luminescence was measured with microplate reader Infinite M200 (TECAN). Compounds with Nrf2 value higher than 1 are more effective than dimethylfumarate (DMF), a strong Nrf2 activator approved for the treatment of psoriasis and multiple sclerosis. All newly developed derivatives are more active than kinetin, a naturally-occurring cytokinin that has been used as a reference substance and is known in the art.

TABLE 7

Activation of transcription factor Nrf2

| Compound | Nrf2 (compound/DMF) |
|---|---|
| kinetin | 0.04 ± 0.00 |
| 155 | 0.24 ± 0.07* |
| 30 | 1.09 ± 0.29 |
| 76 | 0.27 ± 0.15 |
| 89 | 0.19 ± 0.02 |
| 71 | 0.18 ± 0 |
| 116 | 0.24 ± 0.05 |
| 110 | 1.83 ± 0.08 |
| 114 | 2.53 ± 0.39 |
| 150 | 0.34 ± 0.02 |
| 160 | 0.14 ± 0.03 |
| 128 | 0.66 ± 0.14 |
| 66 | 0.25 ± 0.17 |
| 64 | 1.21 ± 0.09 |

*Mean ± SD (n = 3)

Example 46 Inhibition of Intracellular ROS Production by Compound 114

ROS production in living cells was determined by using the fluorescent probe DCFH-DA. In brief, compound 114 at 100, 10, 1 and 0.1 μM concentrations was incubated for 24 h with BJ skin fibroblasts. Thereafter, cells were washed with phosphate buffer and DCFH-DA was added. The fluorescence was read every 1 min over 20 min by using microplate reader Infinite M200 (TECAN, Switzerland). ROS production was calculated as the increase in fluorescence over 20 min. Compound 114 significantly decreased intracellular ROS production in vitro at concentration ≥10 μM.

Example 47 Protection of Peroxidation of Membrane Lipids

A typical symptom associated with aging is the direct consequence of increased concentrations of reactive oxygen species and lipid peroxidation. Therefore, the malondialdehyde (MDA) levels of lipid peroxidation decomposition product were measured in separate wheat leaves which were exposed to the new prepared derivatives and kinetin for four days in the dark as described in Example 7. MDA levels were measured using thiobarbituric acid (TBA method). In detail, 100 mg of fresh plant material is homogenized with 1 ml of 80% methanol in a ball mill (MM301, Retsch, Germany) using a high shaking speed. The crude extract was centrifuged at 10,000×g for 5 minutes and 100 µl aliquots of the supernatant were mixed with 100 µl of 0.5% (w/v) TBA containing 0.1% (w/v) trichloroacetic acid. The resulting solution was then incubated for 30 min at 95° C. The samples were rapidly cooled on ice and centrifuged for 5 minutes at 1000.times.g. The supernatant absorbance was measured at 532 nm with a background reading at 600 nm and the amount of MDA-TBA complex was calculated using an absorbance coefficient (155 mM-1 cm-1). The new derivatives significantly reduced the peroxidation of membrane lipids compared to untreated control (Table 8—values expressing MDA content, membrane lipid degradation product). The compounds of the present invention significantly reduce the peroxidation level of membrane lipids in animal cells, as can be seen from the results in Table 8. The newly prepared derivatives of the general formula thus have a protective function against the negative effects of reactive oxygen species that accumulate strongly in the tissues.

TABLE 8

Influence of new compounds on peroxidation of membrane lipids in NIH3T3 fibroblasts.

| Compound No. | MDA (nmol/g FW) |
|---|---|
| Control | 18.9 (±2.2) |
| kinetin | 14.2 (±1.6) |
| 3 | 12.4 (±1.1) |
| 9 | 12.2 (±1.0) |
| 13 | 13.1 (±1.1) |
| 14 | 11.4 (±1.0) |
| 30 | 12.6 (±1.1) |
| 39 | 11.4 (±1.0) |
| 46 | 11.2 (±1.5) |
| 47 | 12.5 (±1.2) |
| 49 | 12.3 (±1.0) |
| 58 | 11.4 (±0.9) |
| 59 | 11.5 (±1.0) |
| 60 | 12.2 (±1.2) |
| 75 | 11.7 (±1.2) |
| 82 | 10.9 (±0.7) |
| 84 | 10.6 (±0.8) |
| 85 | 11.1 (±0.9) |
| 87 | 10.4 (±1.0) |
| 93 | 10.5 (±1.1) |
| 99 | 10.2 (±0.9) |
| 101 | 10.6 (±0.5) |
| 103 | 10.1 (±0.9) |
| 104 | 9.6 (±0.7) |
| 105 | 10.6 (±0.8) |
| 107 | 10.3 (±0.9) |
| 108 | 9.7 (±0.6) |
| 111 | 10.3 (±1.0) |
| 114 | 8.8 (±0.5) |
| 116 | 9.2 (±0.8) |
| 119 | 9.7 (±0.9) |
| 127 | 10.4 (±1.4) |
| 132 | 10.7 (±1.2) |

*FW—fresh weight

Example 48 Ames Test

The test substance was (114) assayed for the mutagenicity by the Bacterial Reverse Mutation Test. The performed test was based on EU method B.13/14 Mutagenicity—Reverse mutation test using bacteria, which is analogous to the OECD Test Guideline No. 471. Four indicator *Salmonella typhimurium* strains TA 98, TA 100, TA 1535, TA 1537 and one indicator *Escherichia coli* WP2 uvrA strain were used. The test substance was dissolved in dimethylsulfoxide (DMSO) and assayed in doses of 10-1000 µg per plate, which were applied to plates in volume of 0.1 mL. Experiments were performed without as well as with metabolic activation with a supernatant of rat liver and a mixture of cofactors. The working procedure described is in accordance with the documents Method B.13/14, Mutagenicity: Reverse Mutation Test Using Bacteria, Council Regulation (EC) No. 440/2008. Published in O.J. L 142, 2008 and OECD Test Guideline 471, Bacterial Reverse Mutation Test. Adopted Jul. 21, 1997. In the arrangement given above, the test substance was non-mutagenic for all the used tester strains without as well as with metabolic activation.

Example 49 Acute Toxicity—Fixed Dose Procedure (Subcutaneous)

The aim of the study was to investigate acute toxic effects of the test substance, after a single subcutaneous administration to Wistar rats. The testing was performed according to the methods: ČSN EN ISO 10993-11: Biologické hodnoceni zdravotnických prostředků—část 11: Zkoušky na systémovou toxicitu and OECD Test Guideline No. 420 Acute Oral Toxicity—Fixed Dose Procedure. Adopted 17 Dec. 2001. The test substance 114 was administered in a single dose as solution in vehicle (olive oil), given subcutaneously to male and female Wistar rats. The dosing was performed sequentially. The pre-test (the sighting study) was performed with 1 female and 1 male for each dose level. The dose level of 30 mg/kg was used as the starting dose. No death of animal was recorded at the starting dose, therefore the following dose level was used (100 mg/kg). The test substance administered at the dose of 30 and 100 mg/kg caused no death and no clinical signs of intoxication were observed. The presence of subcutaneously administered test substance at the dose level of 30 and 100 mg/kg was visible to second day after application. No macroscopic changes were diagnosed during pathological examination. According to the study results the Maximum Tolerated Dose (subcutaneous) of the test substance for male and female rats is >100 mg/kg.

Example 50 Acute Dermal Toxicity

The test substance 114 was tested for acute dermal toxicity using Wistar rats. Testing was performed according to ČSN EN ISO 10993-11: Biologické hodnoceni zdravotnických prostředků—část 11: Zkoušky na systémovou toxicitu and according to OECD Test Guideline No. 402 Acute Dermal Toxicity Adopted 24 Feb. 1987. The study was performed as limit test: two groups of animals—5 males and 5 females at the dose of 1000 mg/kg of body weight. The pre-test was performed with 1 male and 1 female from each group. After the pilot experiment, the other animals of the group were dosed. The test substance in delivered form was applied on the shaved skin of the test animals for 24 hours. The test animals were observed 14 days after exposure to the test substance, afterwards they were sacrificed, and the necropsy for macroscopic examination of the organs was performed. The test substance applied at the dose of 1000 mg/kg of body weight did not cause death of animals. No clinical signs of toxicity were observed during the whole study. No macroscopic changes were diagnosed during pathological examination. The test substance toxicity was evaluated on the basis of mortality, body weight changes, and clinical signs of toxicity during the observation period and necropsy findings at the end of the study. According to the results of study, the value of Maximum Tolerated Dose (dermal) of the test substance for rats of both sexes is higher than 1000 mg/kg of body weight.

Example 51 In Vitro Skin Irritation Test

Test substance was assayed for the in vitro skin irritation in human epidermal model EpiDerm™. The test was performed according to the Method B.46. In vitro skin irritation: Reconstructed human epidermis model test and Protocol for: In Vitro EpiDerm™ Skin Irritation Test For use with MatTek Corporation's Reconstructed Human Epidermal Model EPI-200-SIT (see par. 1.4, (1), (3)). Two types of extract were prepared by means of polar (water) as well as non-polar extractant (olive oil) according to directions given in ČSN EN ISO 10 993-12 (2012). After pre-incubation of tissues, 30 μl of an extract was placed directly atop to the tissue so it covered all tissue surfaces. Length of exposition was 60 minutes. Three tissues were used for the extract and for each control. The procedure was performed separately for each extract. After removal of extracts of the test substance from tissues, tissues were post incubated for 42 hours due to leave of damage reparation, followed by three hours incubation with MTT and two hours extraction period with shaking. Optical density (OD570) of isopropyl alcohol extracts was measured on a spectrophotometer. Relative cell viability was calculated for each tissue as % of the mean viability of the negative control tissues. Under the above-described experimental design, average viability of tissues treated by test substance water extract was 99.0% and by test substance olive oil extract 103.0%, i.e. viability was >50% in both cases. The effect of the test substance 114 was negative in EpiDerm™ model (tissues were not damaged). According to the classification criteria given in chapter 4.5, the test substance is considered to have no category in regard to skin irritation.

Example 52 Animal Skin Irritation Test

The test substance 114 was tested in Animal skin irritation test. Rabbits (New Zealand Albino breed) were used for the test. The test was performed according to ČSN EN ISO 10993 (Březen 2014): Biologické hodnoceni zdravotnických prostředků—část 10: Zkoušky dráždivosti a senzibilizace kůže, článek 6.3 Zkouška dráždivosti na zvířatech (Biological evaluation of medical devices—Part 10: Tests for irritation and delayed-type hypersensitivity). A dose 0.5 g of the test substance was applied to the skin of the back on each side of each rabbit. In order to demonstrate the sensitivity of the assay, positive control (0.5 g of lauryl sulfate) was included. At first the one rabbit (test animal. No. 16) was used. Two other rabbits (rabbit No. 17 and No. 18) were used in confirmatory test. At the end of the contact time (4 hours) the dressings were removed and animals were examined for signs of erythema and oedema, and the response was evaluated at 1, 24, 48 and 72 hours afterpatches removal. No changes in animal weights were observed. No clinical signs of systemic intoxication were detected during the whole study. Primary Irritation Index for positive control was 1.67 (slight). The reliability of positive control was ensured. No erythema and oedema were recorded at 1, 24, 48 and 72 hours in test sites in all three rabbits. Primary Irritation Index for test substance was defined as 0. No skin irritation was caused by 4-hour exposure of rabbits to test substance.

Example 53 Formulations

The growth regulatory formulations usually contain from 0.1 to 99% by weight, especially from 0.1 to 95% by weight, of active ingredient mixture comprising the $N^2,N^6$-disubstituted-9-(2-oxacycloalkyl)-9H-purine-2,6-diamine derivative of this invention, from 1 to 99.9% by weight of a solid or liquid formulation adjuvant, and from 0 to 25% by weight, especially from 0.1 to 25% by weight, of a surfactant. Whereas commercial products are usually formulated as concentrates, the end user will normally employ dilute formulations. The compositions may also comprise further ingredients, such as stabilizers, e.g., vegetable oils or epoxidised vegetable oils (epoxidised coconut, rapeseed oil or soybean oil), antifoams, e.g., silicone oil, preservatives, viscosity regulators, binders, tackifiers, and also fertilisers or other active ingredients. Preferred formulations have especially the following compositions: (%=percent by weight):

| Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 2% | — | 2% |
| cyclohexanone | — | — | 10% | 20% |
| aromatic hydrocarbon mixture (C9-C12) | 83% | 82% | 53% | 18% |

Emulsions of any desired concentration can be obtained from such concentrates by dilution with water.

| Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol (MW 400) | 20% | 10% | — | — |
| N-methyl-2-pyrrolidone | — | — | 30% | 10% |
| aromatic. hydrocarbon mixture 9C$_9$-C$_{12}$) | 75% | 60% | — | — |

The solutions are suitable for use in the form of microdrops.

| Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 87% | 61% | 37% | — |

The active ingredient is mixed thoroughly with the adjuvants and the mixture is thoroughly ground in a suitable mill, affording wettable powders which can be diluted with water to give suspensions of any desired concentration.

| Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 86% | 78% | 64% | 38% |

The finely ground active ingredient is intimately mixed with the adjutants, giving a suspension concentrate from which suspensions of any desired concentration can be obtained by dilution with water.

Dry Capsules 5000 capsules, each of which contain 0.25 g of one of the $N^2,N^6$-disubstituted-9-(2-oxacycloalkyl)-9H-purine-2,6-diamine derivative as active ingredient, are prepared as follows:

Composition: Active ingredient: 1250 g; Talc: 180 g; Wheat starch: 120 g; Magnesium stearate: 80 g; Lactose 20 g.

Preparation process: The powdered substances mentioned are pressed through a sieve of mesh width 0.6 mm. Portions of 0.33 g of the mixture are transferred to gelatine capsules with the aid of a capsule-filling machine.

Soft Capsules 5000 soft gelatine capsules, each of which contain 0.05 g of one of the $N^2,N^6$-disubstituted-9-(2-oxacycloalkyl)-9H-purine-2,6-diamine derivative as active ingredient, are prepared as follows:

Composition: 250 g Active ingredient+2 litres Lauroglycol

Preparation process: The powdered active ingredient is suspended in Lauroglykol® (propylene glycol laurate, Gattefossé S. A., Saint Priest, France) and ground in a wet-pulveriser to a particle size of about 1 to 3 mm. Portions of 0.419 g of the mixture are then transferred to soft gelatine capsules by means of a capsule-filling machine.

Soft Capsules 5000 soft gelatine capsules, each of which contain 0.05 g of one of the $N^2,N^6$-disubstituted-9-(2-oxacycloalkyl)-9H-purine-2,6-diamine derivative as active ingredient, are prepared as follows:

Composition: 250 g Active ingredient+1 litre PEG 400+1 litre Tween 80

Preparation process: The powdered active ingredient is suspended in PEG 400 (polyethylene glycol of Mr in the range of from 380 to about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of 0.43 g of the mixture are then transferred to soft gelatine capsules by means of a capsule-filling machine.

Example 54 Gel Formulation

An ointment formulation was tested during a pilot clinical study with 4 volunteers with psoriatic skin disorders. The components are given in grams per 100 g.

| Compound | Content |
|---|---|
| Compound 114 | 1.0 g |
| Butylhydroxytoluenum | 0.2 g |
| Butylparaben | 0.2 g |
| Diethyleneglycol monoethyl ether | 10.0 g |
| Silica colloidalis anhydrica | 5.0 g |
| Propylene glycol laurate | 83.6 g |

The gel consistence may be additionally modified by addition of silica colloidalis anhydrica. It is again expected that the transdermal Transcutol P/Lauroglycol FCC system will increase the efficiency of compound 114. Silica colloidalis anhydrica will probably slow down the penetration of the active substance.

Example 55 Preparation Procedure of a Skin Ointment

The formulation components are given in grams per 200 g:

| Compound | Content |
|---|---|
| Compound 114 | 2.0 g |
| Butylhydroxytoluenum | 0.4 g |
| Butylparaben | 0.4 g |
| Diethyleneglycol monoethyl ether | 20.0 g |
| Glycerol dibehenate | 44.0 g |
| Propylene glycol laurate | 133.2 g |

Recommended Procedure

Phase A: 2 grams of $N^2,N^6$-disubstituted-9-(2-oxacycloalkyl)-9H-purine-2,6-diamine derivative 114 were dissolved in 20 g of Transcutol P while stirring continuously at room temperature in a separate glass or stainless-steel container. The dissolution process may be accelerated by heating the solution to a maximal temperature of 40° C.

Phase B: 0.4 grams of Nipanox BHT and 0.4 g of Nipabutyl were dissolved while stirring continuously in 133.2 g of Lauroglycol FCC at a temperature of approximately 70° C. in another separate glass or stainless-steel container. The clear oily solution is heated to a temperature of approximately 80° C. and 44 g of Compritol 888 ATO are melted in it while stirring continuously. The clear oily solution is cooled down to approximately 60° C. and during continuous stirring and cooling down is mixed with phase A. The resulting whitish ointment-like substance is divided into approximately 15 gram portions and filled into prearranged plastic containers.

Example 56 Formulation of a Composition for Topical Application to the Skin

A composition for topical application to the skin contains the following ingredients by weight %:

| | |
|---|---|
| Active ingredient: | |
| Compound 114 | 0.1% |
| Oil phase: | |
| Cetyl alcohol | 5.0% |
| Glyceryl monostearate | 15.0% |
| Sorbitan monooleate | 0.3% |
| Polysorbate 80 USP | 0.3% |

-continued

Aqueous phase:

| | |
|---|---|
| Methylcellulose 100 cps | 1.0% |
| Methyl paraben | 0.25% |
| Propyl paraben | 0.15% |
| Purified water | q.s. to 100% |

Methyl paraben and propyl paraben were dissolved in hot water and subsequently methylcellulose was dispersed in the hot water. The mixture was chilled at 60° C. until the methylcellulose dissolved. The mixture was then heated to 72° C. and added to the oil phase which was heated to 70° C. while stirring continuously. $N^2,N^6$-disubstituted-9-(2-oxacycloalkyl)-9H-purine-2,6-diamine derivative 114 was added at a temperature of 35° C. and the resulting mixture was stirred continuously until dispersed. This composition is applied to the skin on at least a daily basis until the desired skin-ameliorating (anti-aging) effect is reached.

The invention claimed is:

1. $N^2,N^6$-disubstituted-9-(2-oxacycloalkyl)-9H-purine-2,6-diamine derivatives of the general formula I,

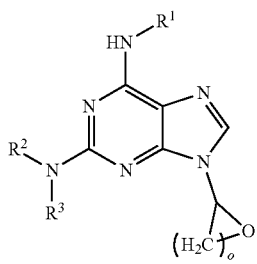

wherein
$R^2$ and $R^3$ are independently selected from the group consisting of H, —$(CH_2)_mCH_3$, m=0 or 1 or 2, —$CH_2(CH_3)_2$, and —$(CH_2)_n$—$N(CH_3)_2$, n=2 or 3, wherein at least one of $R^2$ and $R^3$ is alkyl or dimethylaminoalkyl;
o is an integer in the range of from 2 to 5, wherein a hydrogen in at least one methylene group ($CH_2$) of the substituent on N atom in position 9 may optionally be replaced by a methyl or methoxy group;
$R^1$ is selected from the group consisting of
furfuryl or furfuryl substituted with at least one methyl or methoxy group,
benzyl or benzyl substituted by at least one substituent selected from the group consisting of methyl, trifluoromethyl, hydroxy, methoxy, trifluoromethoxy, halogen, amino, methoxycarbonyl and acetoxy,
3-methylbut-2-en-1-yl,
3-methylbut-3-en-1-yl,
(4-hydroxy-3-methylbut-2-en-1-yl, and
4-hydroxy-3-methylbutyl;
or a pharmaceutically acceptable salt thereof with an alkali metal, ammonium or amine, in the form of a racemate or optically active isomer, or an addition salt with acid.

2. $N^2,N^6$-disubstituted-9-(2-oxacycloalkyl)-9H-purine-2,6-diamine derivatives according to claim 1, wherein if $R^2$ or $R^3$ is —$(CH_2)_nN(CH_3)_2$, the other of these substituents is hydrogen.

3. $N^2,N^6$-disubstituted-9-(2-oxacycloalkyl)-9H-purine-2,6-diamine derivatives according to claim 1, wherein the group —$N(R^2)(R^3)$ is selected from the group consisting of methylamino, ethylamino, propylamino, 2-propylamino, dimethylamino, diethylamino, [2-(dimethylamino)ethyl]amino; and [3-(dimethylamino)propyl]amino.

4. $N^2,N^6$-disubstituted-9-(2-oxacycloalkyl)-9H-purine-2,6-diamine derivatives according to claim 1, wherein R1 is selected from the group consisting of furfuryl, 3-methylfurfuryl, 4-methylfurfuryl, 5-methylfurfuryl, 3-methoxyfurfuryl, 4-methoxyfurfuryl, 5-methoxyfurfuryl, benzyl, 2-methylbenzyl, 3-methylbenzyl, 4-methylbenzyl, 2-(trifluoromethyl)benzyl, 3-(trifluoromethyl)benzyl, 4-(trifluoromethyl)benzyl, 2-hydroxybenzyl, 3-hydroxybenzyl, 4-hydroxybenzylamino, 2-methoxybenzyl, 3-methoxybenzyl, 4-methoxybenzyl, 2-(trifluoromethoxy)benzyl, 3-(trifluoromethoxy)benzyl, 4-(trifluoromethoxy)benzyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 2-iodobenzyl, 3-iodobenzyl, 4-iodobenzyl, 2-aminobenzyl, 3-aminobenzyl, 4-aminobenzyl, 2-(methoxykarbonyl)benzyl, 3-(methoxykarbonyl)benzyl, 4-(methoxykarbonyl)benzyl, 2-acetoxybenzyl, 3-acetoxybenzyl, 4-acetoxybenzyl, 2,3-dihydroxybenzyl, 2,5-dihydroxybenzyl, 3,4-dihydroxybenzyl, 3,5-dihydroxybenzyl, 2,3-dimethoxybenzyl, 2,5-dimethoxybenzyl, 3,4-dimethoxybenzyl, 3,5-dimethoxybenzyl, 2,6-difluorobenzyl, 3,4-difluorobenzyl, 3,5-difluorobenzyl, 2,3-dichlorobenzyl, 2,4-dichlorobenzyl, 3,4-dichlorobenzyl, 3,5-dichlorobenzyl, 2-hydroxy-3-methylbenzyl, 2-hydroxy-5-methylbenzyl, 2-hydroxy-3-methoxybenzyl, 2-hydroxy-4-methoxybenzyl, 3-hydroxy-4-methoxybenzyl, 4-hydroxy-2-methoxybenzyl, 4-hydroxy-3-methoxybenzyl, 3-fluoro-4-hydroxybenzyl, 3-chloro-4-hydroxybenzyl, 4-fluoro-3-hydroxybenzyl, 4-chloro-3-hydroxybenzyl, 2-chloro-4-fluorobenzyl, 2-chloro-6-fluorobenzyl, 3,4,5-trihydroxybenzyl, 3,4,5-trimethoxybenzyl, 2,3,4-trifluorobenzyl, 2,3,6-trifluorobenzyl, 3,4,5-trifluorobenzyl, 4-hydroxy-3,5-dimethoxybenzyl, 3-methylbut-2-en-1-yl, 3-methylbut-3-en-1-yl, 4-hydroxy-3-methylbut-2-en-1-yl, and 4-hydroxy-3-methylbutyl.

5. $N^2,N^6$-disubstituted-9-(2-oxacycloalkyl)-9H-purine-2,6-diamine derivatives according to claim 1, wherein the substituent on N atom in position 9 is selected from tetrahydro-2H-pyran-2-yl and tetrahydrofuran-2-yl, which may optionally be substituted by at least one methyl or methoxy group.

6. The $N^2,N^6$-disubstituted-9-(2-oxacycloalkyl)-9H-purine-2,6-diamine derivatives according to claim 1, selected from the group consisting of 2-(methylamino)-6-furfurylamino-9-(tetrahydrofuran-2-yl)-9H-purine, 2-(ethylamino)-6-furfurylamino-9-(tetrahydrofuran-2-yl)-9H-purine; 2-(dimethylamino)-6-furfurylamino-9-(tetrahydrofuran-2-yl)-9H-purine; 2-(diethylamino)-6-furfurylamino-9-(tetrahydrofuran-2-yl)-9H-purine; 2-{[2-(dimethylamino)ethyl]amino}-6-furfurylamino-9-(tetrahydrofuran-2-yl)-9H-purine; 2-(methylamino)-6-furfurylamino-9-(tetrahydro-2H-pyran-2-yl)-9H-purine, 2-(ethylamino)-6-furfurylamino-9-(tetrahydro-2H-pyran-2-yl)-9H-purine; 2-(dimethylamino)-6-furfurylamino-9-(tetrahydro-2N-pyran-2-yl)-9H-purine; 2-(diethylamino)-6-furfurylamino-9-(tetrahydro-2H-pyran-2-yl)-9H-purine; and 2-{[2-(dimethylamino)ethyl]amino}-6-furfurylamino-9-(tetrahydro-2H-pyran-2-yl)-9H-purine, or a salt thereof, wherein the furfuryl group can optionally be substituted by at least one substituent selected from the group consisting of methyl and methoxy group.

7. A method for inhibiting lipid and protein peroxidation and/or inhibiting aging processes comprising the step of providing $N^2,N^6$-disubstituted-9-(2-oxacycloalkyl)-9H-purine-2,6-diamine derivatives of the general formula I,

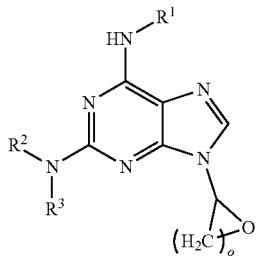

wherein
- $R^2$ and $R^3$ are independently selected from the group consisting of H, $-(CH_2)_mCH_3$, m=0 or 1 or 2, $-CH_2(CH_3)_2$, and $-(CH_2)_n-N(CH_3)_2$, n=2 or 3, wherein at least one of $R^2$ and $R^3$ is alkyl or dimethylaminoalkyl;
- o is an integer in the range of from 2 to 5, wherein a hydrogen in at least one methylene group ($CH_2$) of the substituent on N atom in position 9 may optionally be replaced by a methyl or methoxy group;
- $R^1$ is selected from the group consisting of
  furfuryl or furfuryl substituted with at least one methyl or methoxy group,
  benzyl or benzyl substituted by at least one substituent selected from the group consisting of methyl, trifluoromethyl, hydroxy, methoxy, trifluoromethoxy, halogen, amino, methoxycarbonyl and acetoxy,
  3-methylbut-2-en-1-yl,
  3-methylbut-3-en-1-yl,
  (4-hydroxy-3-methylbut-2-en-1-yl, and
  4-hydroxy-3-methylbutyl;
- or a pharmaceutically acceptable salt thereof with an alkali metal, ammonium or amine, in the form of a racemate or optically active isomer, or an addition salt with acid to a subject in need thereof.

8. The method according to claim 7, wherein the method comprises treatment of psoriasis or multiple sclerosis.

9. The method according to claim 7, wherein the method comprises stimulation of proliferation, morphogenesis and senescence inhibition, cell division and differentiation factors of plant, mammal, microorganisms, yeast and fungal cells.

10. Pharmaceutical composition, characterized in that it comprises at least one $N^2,N^6$-disubstituted-9-(2-oxacycloalkyl)-9H-purine-2,6-diamine derivative of the general formula I according to claim 1, and at least one auxiliary substance.

11. A cosmetic composition, characterized in that it comprises at least one $N^2,N^6$-disubstituted-9-(2-oxacycloalkyl)-9H-purine-2,6-diamine derivative of the general formula I according to claim 1, and at least one auxiliary substance.

12. $N^2,N^6$-disubstituted-9-(2-oxacycloalkyl)-9H-purine-2,6-diamine derivatives according to claim 1, wherein the substituent on N atom in position 9 is selected from tetrahydro-2H-pyran-2-yl and tetrahydrofuran-2-yl, which may optionally be substituted by one methyl or methoxy group.

* * * * *